(12) United States Patent
Kitajima et al.

(10) Patent No.: US 8,956,289 B2
(45) Date of Patent: Feb. 17, 2015

(54) VITAL INFORMATION MEASURING DEVICE

(75) Inventors: Kazumi Kitajima, Higashiosaka (JP);
Yoshiroh Nagai, Nishinomiya (JP);
Norio Ishikawa, Osaka (JP); Koji Yamamoto, Kawanishi (JP)

(73) Assignee: Konica Minolta Sensing, Inc. (JP)

( * ) Notice: Subject to any disclaimer, the term of this patent is extended or adjusted under 35 U.S.C. 154(b) by 1392 days.

(21) Appl. No.: 11/545,294

(22) Filed: Oct. 10, 2006

(65) Prior Publication Data

US 2007/0123756 A1    May 31, 2007

(30) Foreign Application Priority Data

Oct. 14, 2005 (JP) .................................. 2005-300610

(51) Int. Cl.
*A61B 5/00* (2006.01)
*A61B 5/1455* (2006.01)
*A61B 8/00* (2006.01)
(Continued)

(52) U.S. Cl.
CPC ........... *A61B 5/6833* (2013.01); *A61B 5/14552* (2013.01); *A61B 5/6826* (2013.01); *A61B 5/6838* (2013.01); *A61B 8/4236* (2013.01);
(Continued)

(58) Field of Classification Search
CPC ............ A61B 5/04087; A61B 5/6832–5/6833; A61B 5/688; A61B 8/4236; A61B 5/4806–5/4818; A61B 2560/0412; A61B 5/0531; A61B 5/441; A61B 5/6824; A61B 5/6831; G01K 13/002; A63B 2024/0065; A63B 24/0062; G06F 19/30; G06F 19/322; G06F 19/3418

USPC ......... 600/300–301, 310–344, 509, 529, 534, 600/595

See application file for complete search history.

(56) References Cited

U.S. PATENT DOCUMENTS 4,681,118 A * 7/1987 Asai et al. ..................... 600/387
4,862,521 A * 9/1989 Mann ............................... 2/160
(Continued)

FOREIGN PATENT DOCUMENTS

JP          1-117302 U     8/1989
JP          8-154903 A     6/1996
(Continued)

OTHER PUBLICATIONS

Japanese Notice of Reasons for Rejection dated Jun. 22, 2010, for counterpart Japanese Application No. 2005-300610, together with an English translation thereof.

*Primary Examiner* — William Thomson
*Assistant Examiner* — Shirley Jian
(74) *Attorney, Agent, or Firm* — Cantor Colburn LLP

(57) ABSTRACT

A vital information measuring device includes: a flexible substrate including a functioning part which is mounted thereon; and an outer member for covering the flexible substrate. The functioning part has: a sensor section for sequentially measuring a parameter relating to certain vital information on a subject; a circuit section for performing a predetermined process with respect to a measurement signal outputted from the sensor section; a memory section for storing therein the measurement signal or measurement data after the process by the circuit section; a display section for displaying thereon certain information relating to the measurement; and a power source section for supplying a drive voltage to the respective sections of the functioning part.

12 Claims, 25 Drawing Sheets

(51) Int. Cl.
*A61B 5/087* (2006.01)
*A61B 5/113* (2006.01)

(52) U.S. Cl.
CPC ............. *A61B5/0002* (2013.01); *A61B 5/0878* (2013.01); *A61B 5/1135* (2013.01); *A61B 2560/0412* (2013.01)
USPC ........................................................ 600/301

(56) References Cited

U.S. PATENT DOCUMENTS

| | | | | |
|---|---|---|---|---|
| 4,974,591 | A * | 12/1990 | Awazu et al. ................. | 600/344 |
| 5,246,003 | A | 9/1993 | DeLonzor ..................... | 128/633 |
| 5,638,832 | A * | 6/1997 | Singer et al. ................... | 128/899 |
| 6,018,673 | A * | 1/2000 | Chin et al. ..................... | 600/322 |
| 6,686,843 | B2 * | 2/2004 | Felkowitz .................. | 340/573.1 |
| 6,847,913 | B2 * | 1/2005 | Wigley et al. .................. | 702/131 |
| 6,997,882 | B1 * | 2/2006 | Parker et al. ................... | 600/534 |
| 7,283,850 | B2 * | 10/2007 | Granovetter et al. ......... | 455/570 |
| 7,403,808 | B2 * | 7/2008 | Istvan et al. ................... | 600/393 |
| 7,598,878 | B2 * | 10/2009 | Goldreich .................. | 340/573.1 |
| 7,652,188 | B2 * | 1/2010 | Levanon et al. ................. | 602/41 |
| 7,869,849 | B2 * | 1/2011 | Ollerdessen et al. .......... | 600/323 |
| 8,157,731 | B2 * | 4/2012 | Teller et al. ................. | 600/301 |
| 2002/0038082 | A1 | 3/2002 | Chin ............................ | 600/323 |
| 2003/0069714 | A1 * | 4/2003 | Wigley et al. ................. | 702/131 |
| 2003/0153824 | A1 * | 8/2003 | Tsubata ....................... | 600/407 |
| 2003/0181817 | A1 | 9/2003 | Mori ............................ | 600/500 |
| 2006/0155183 | A1 * | 7/2006 | Kroecker et al. ............. | 600/391 |
| 2006/0258959 | A1 | 11/2006 | Sode ............................ | 600/584 |
| 2009/0177067 | A1 | 7/2009 | Sode ............................ | 600/347 |

FOREIGN PATENT DOCUMENTS

| | | |
|---|---|---|
| JP | 9-128660 A | 5/1997 |
| JP | 9-201338 A | 8/1997 |
| JP | 11-506629 A | 6/1999 |
| JP | 2003-514606 A | 4/2003 |
| JP | 2004-16571 A | 1/2004 |
| JP | 2004-49579 A | 2/2004 |
| WO | WO 2005/023111 A1 | 3/2005 |

* cited by examiner

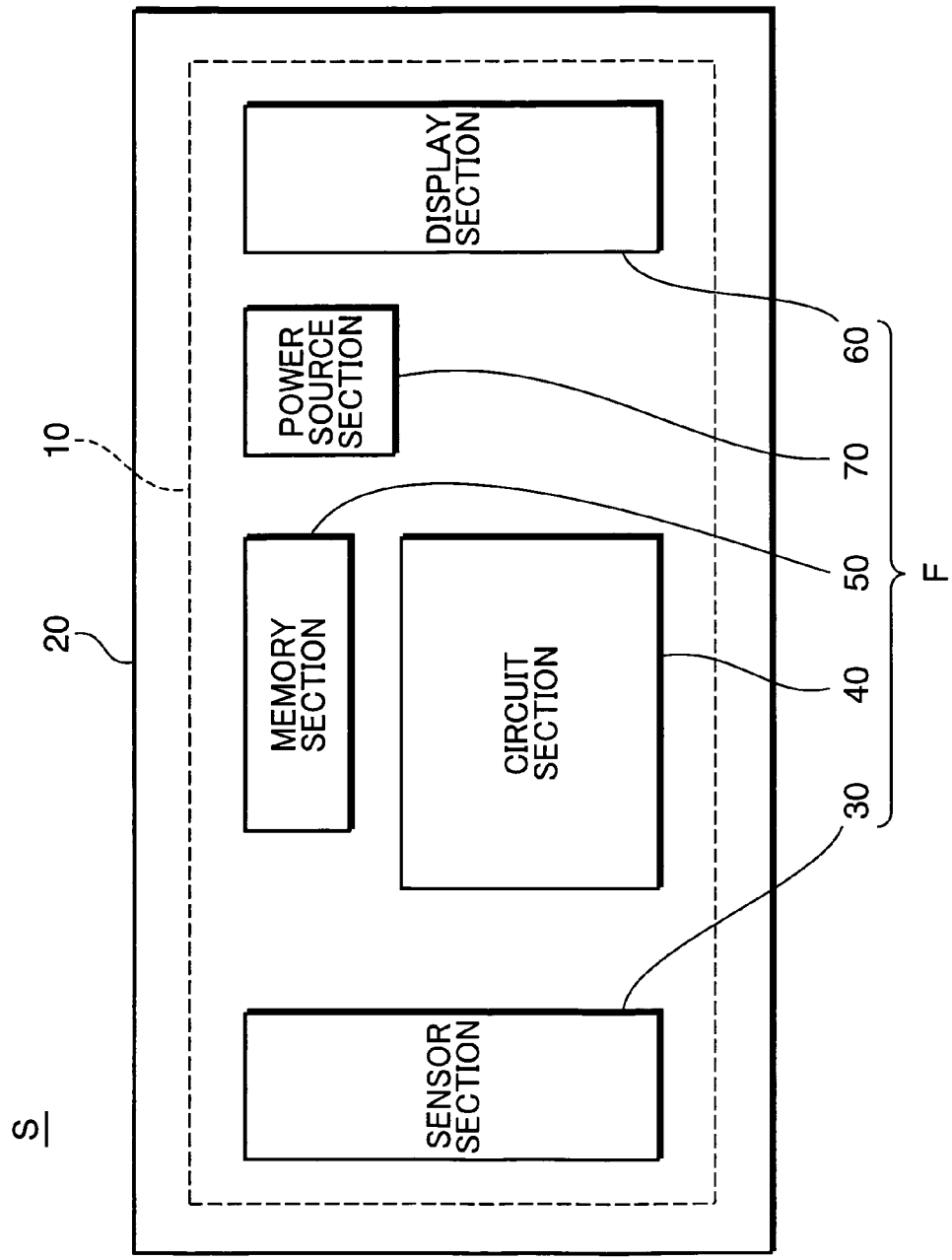

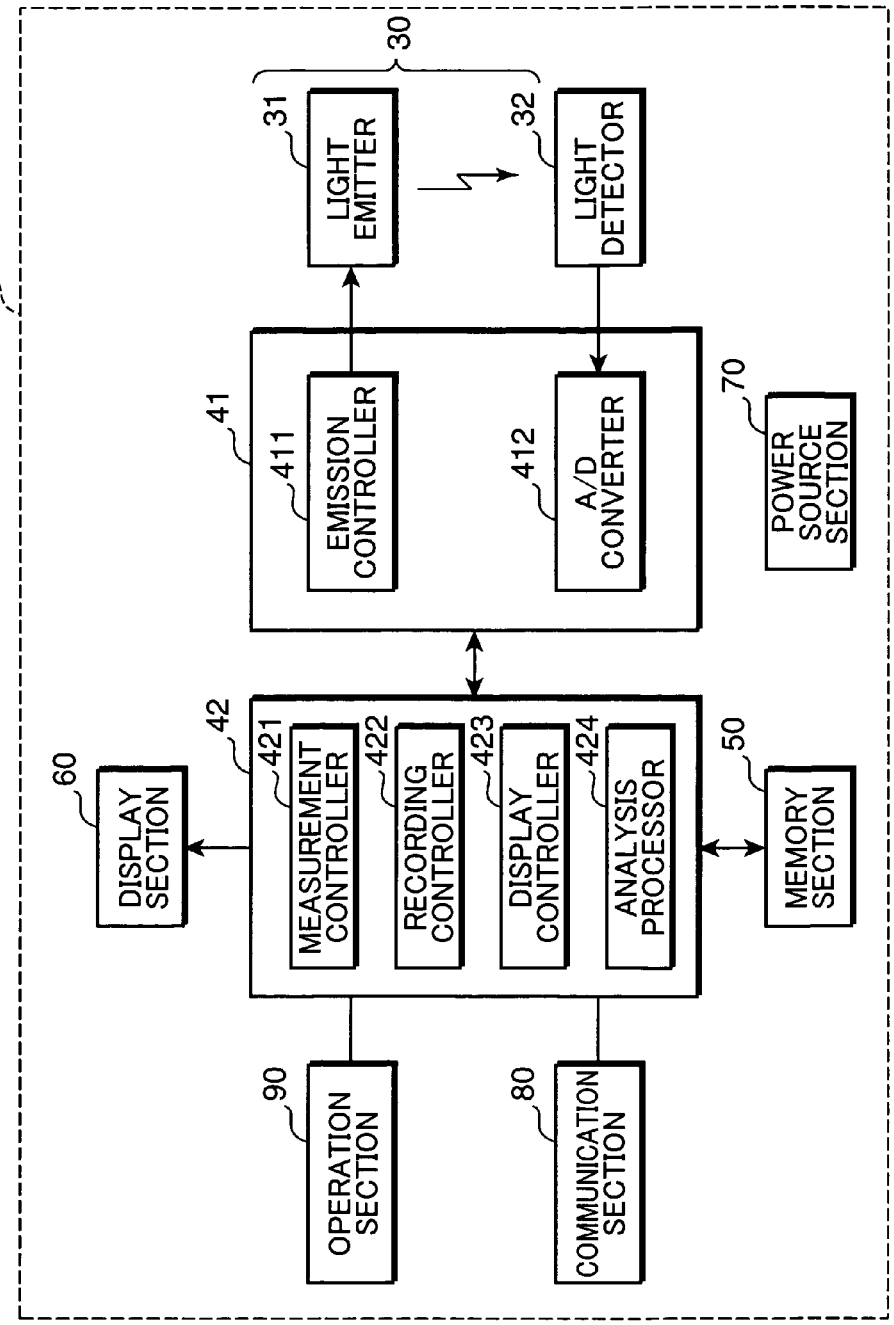

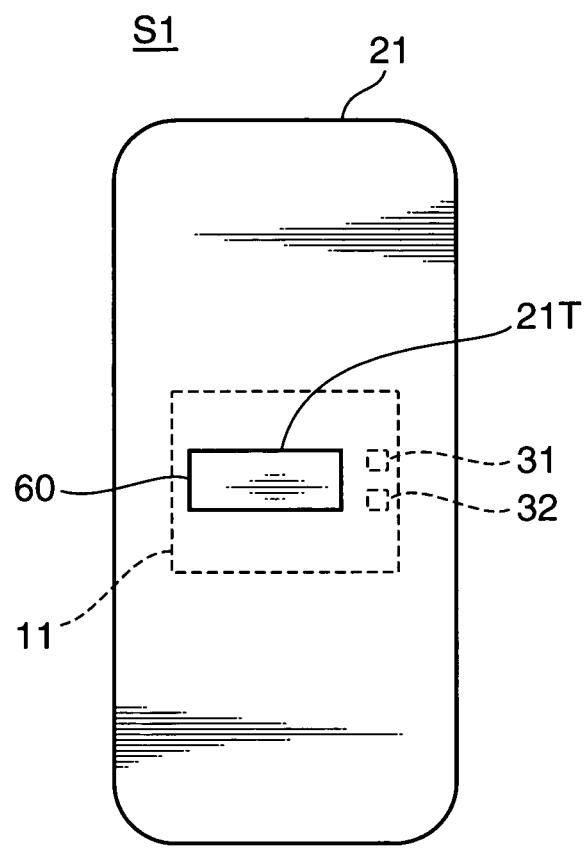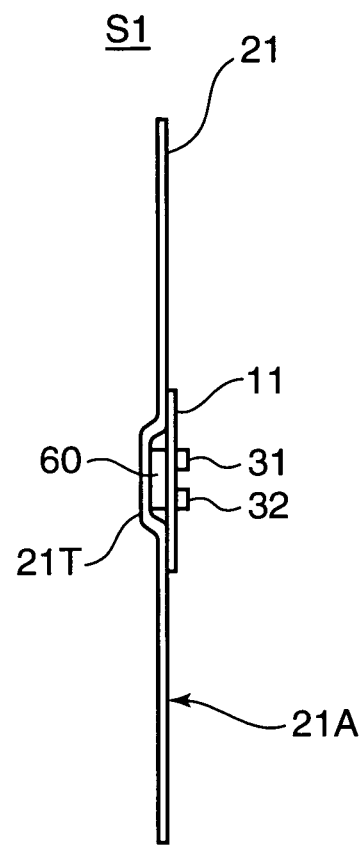

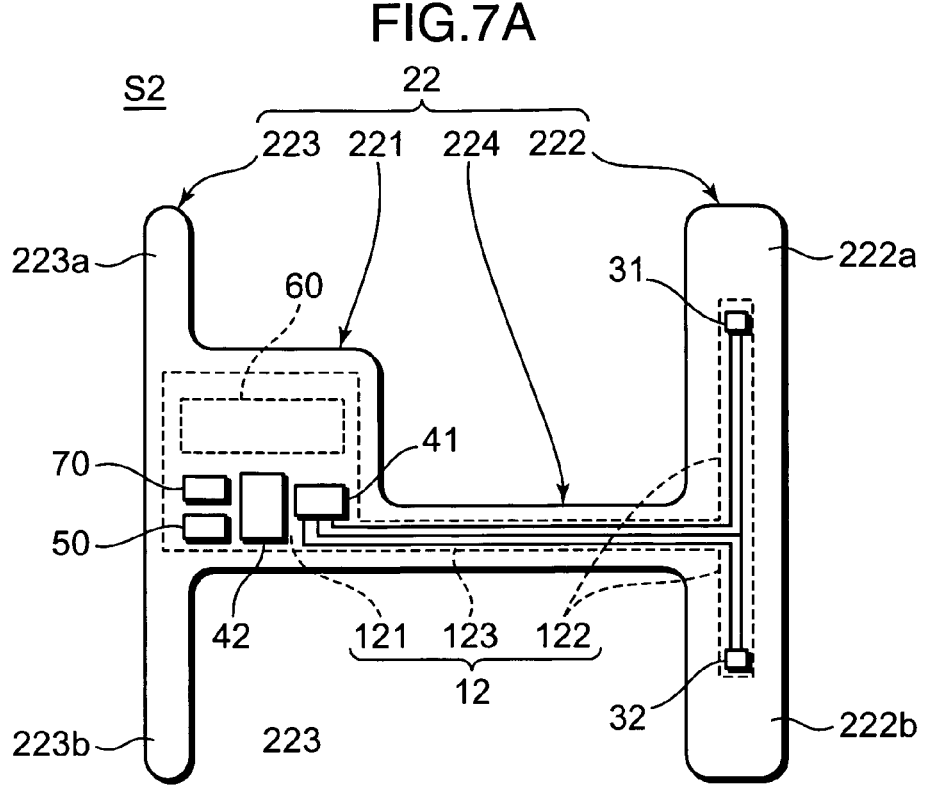
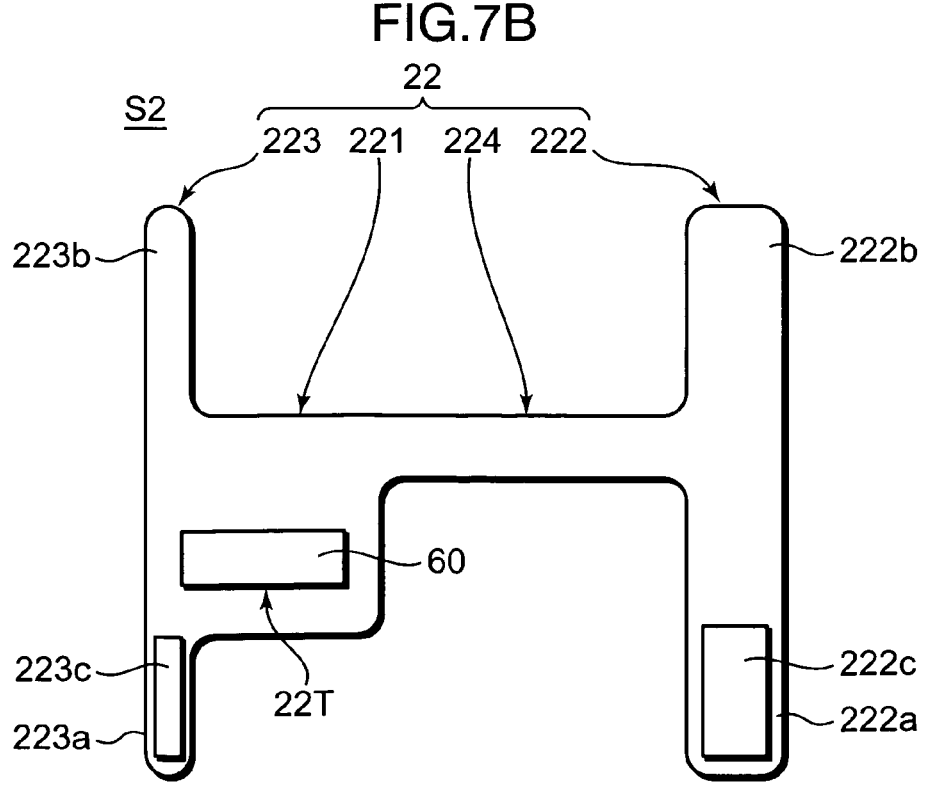

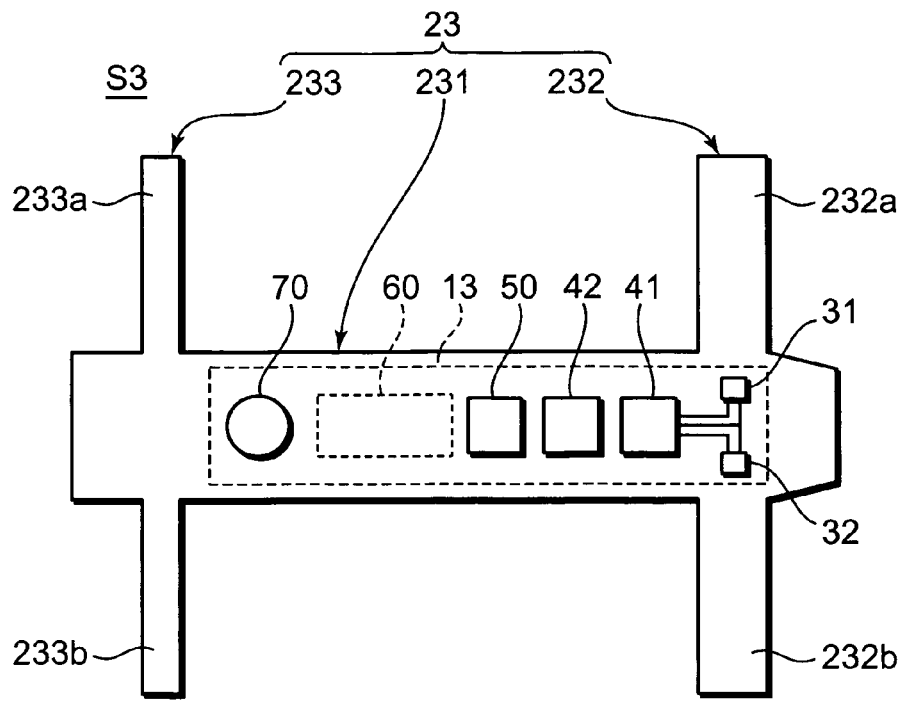
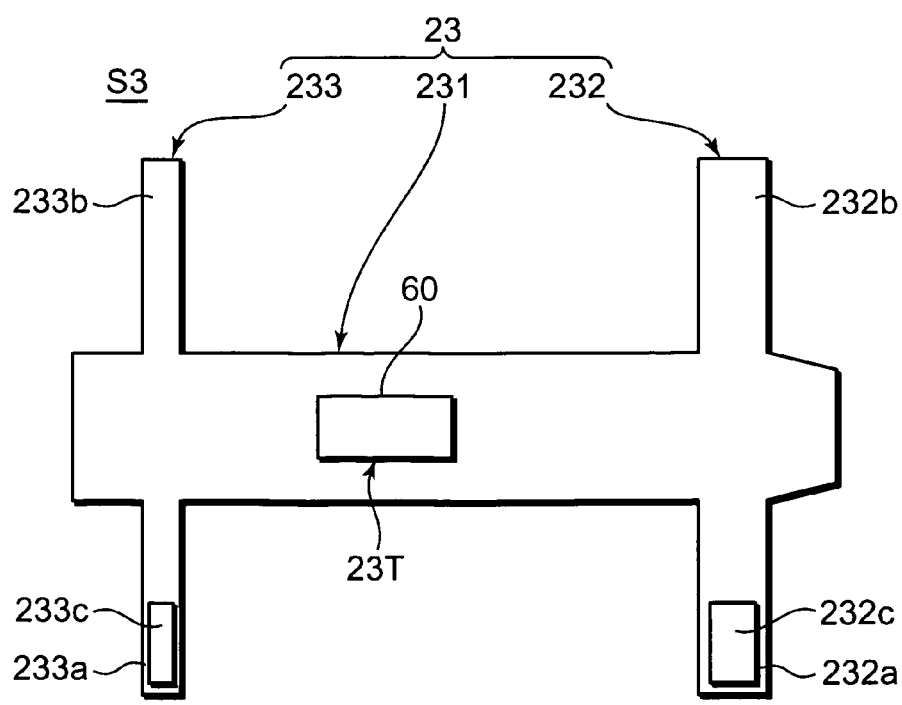

VITAL INFORMATION MEASURING DEVICE

This application is based on Japanese Patent Application No. 2005-300610 filed on Oct. 14, 2005, the contents of which are hereby incorporated by reference.

BACKGROUND OF THE INVENTION

1. Field of the Invention

The present invention relates to a vital information measuring device for non-invasively detecting various vital information from a human body, and more particularly to a vital information measuring device adapted to measure vital information for a long time.

2. Description of the Related Art

There are known a pulse oximeter, a PSG (polysomnography), and a holter monitor, as examples of a vital information measuring device for non-invasively detecting vital information from a human body, particularly, as a vital information measuring device requiring a long time vital information detection. As shown in FIG. 25, a pulse oximeter 100 is used in such a manner that: a probe 101 equipped with a light emitter and a light detector is detachably attached to a finger of a living body i.e. a subject; light is projected onto a living body of the subject i.e. a finger of the subject to be measured to measure a change in the amount of light transmitted through the living body as a pulse signal; and a change in blood oxygen saturation with time during the subject's sleep is obtained by performing moving-averaging with respect to measurement values at each sampling frequency. The pulse oximeter 100 is constructed in such a manner that the probe 101 and a device main body 102 as individual components are electrically connected by a cable 103. Generally, the pulse oximeter 100 is detachably attached to the subject by attaching the device main body 102 around a wrist of the subject by way of a wristband 104, and by securely holding a fingertip of the subject by the probe 101, with the cable 103 extending along the back of the subject's hand.

The PSG is provided with various sensor devices for detecting, in addition to the blood oxygen saturation, various assessment parameters such as pulse waveforms, air flow rates through mouth or nose, snoring sounds, body positions/body movements, chest and abdominal movements in respiration, and electrocardiographic waveforms. The PSG is a measuring device for diagnosing sleep apnea syndrome (SAS) or the like by analysis and display of the measurement results. Similarly to the pulse oximeter, the PSG is composed of a device main body and the various sensor devices which are provided independently of each other. Generally, the device main body of the PSG device is detachably attached to or around the body trunk portion of a subject; and the sensor devices, which are detachably attached to their appropriate sites of the subject, and the device main body are electrically connected by way of cables.

The holter monitor is generally composed of electrodes for detecting an action potential of the subject's heart, and a receiver for receiving data detected from the electrodes. The holter monitor is a measuring device for performing data measurement under a condition that the subject performs a normal activity for one day or so, with five or so electrodes being attached to the chest of the subject, and the receiver being mounted on the waist of the subject. After the measurement completion, the data stored in the receiver is outputted to a predetermined analyzer for an electrocardiographic waveform analysis, so that a time interval (RR-interval) between two consecutive R waves of the electrocardiogram, or the like is obtained. Generally, the electrodes and the receiver are connected by cables. There is also known a cordless measuring device which is constructed to perform radio communication between electrodes and a receiver.

Also, there is known a disposable pulse oximeter, in which solely a sensor device provided with a light emitter and a light receiver is mounted on a flexible substrate for pulse oximetry measurement. There is also known a vital information measuring device, wherein a sensor which is attached to a subject for detecting vital information on the subject has a radio transmitting function, and the measuring device has a controller for controlling an operation of the sensor, and receiving the vital information sent from the sensor.

The pulse oximeter or the PSG has the cable e.g. the cable 103 shown in FIG. 25 for electrically connecting the sensor device to the device main body. These measuring devices are required to be attached to the subject continuously for a long time during his or her sleep. However, if the cable gets hung up in a bedding item or the like, the sensor device may be detached from the attached site of the subject. Also, the subject may feel discomfort or stress because the measuring device is attached to the subject's body, with the cable entangled. Particularly, since the PSG has a large number of sensor devices, the subject may even feel difficulty in rolling over in his or her sleep, which may inhibit good sleep, and resultantly fail to obtain accurate measurement data. The same drawback is involved in the former conventional arrangement i.e. the disposable pulse oximeter, because the flexible substrate for mounting the sensor device thereon, and the oximeter main body are connected by the cable.

The cordless holter monitor and the latter conventional arrangement i.e. the cordless vital information measuring device are free from the drawback that the cable may get hung up. However, the holter monitor and the cordless vital information measuring device have drawbacks that the subject has to carry the receiver for wirelessly receiving a detection signal from the electrodes, and to carry the controller for wirelessly receiving the vital information detected by the sensor, respectively. In both of the cases, despite the cordless arrangement, the subject may feel stress resulting from carrying some parts of the measuring device. Also, these arrangements essentially fail to solve the inconvenience due to the fact that the sensor device and the device main body are provided independently of each other.

SUMMARY OF THE INVENTION

In view of the above problems residing in the conventional examples, it is an object of the present invention to provide a vital information measuring device which is suitable for a long time vital information measurement, with no or less stress to a subject involved in wearing the device, and has an enhanced operability.

An aspect of the invention is directed to a vital information measuring device including: a flexible substrate including a functioning part which is mounted thereon; and an outer member for covering the flexible substrate. The functioning part has: a sensor section for sequentially measuring a parameter relating to certain vital information on a subject; a circuit section for performing a predetermined process with respect to a measurement signal outputted from the sensor section; a memory section for storing therein the measurement signal or measurement data after the process by the circuit section; a display section for displaying thereon certain information relating to the measurement; and a power source section for supplying a drive voltage to the respective sections of the functioning part.

These and other objects, features and advantages of the present invention will become more apparent upon reading the following detailed description along with the accompanying drawing.

BRIEF DESCRIPTION OF THE DRAWINGS

FIG. 1 is a plan view briefly showing an arrangement of a vital information measuring device according to an embodiment of the invention.

FIG. 2 is a block diagram showing an electrical configuration of a functioning part to be mounted on a flexible substrate in the case where a pulse oximeter is provided as an example of the inventive vital information measuring device.

FIGS. 3A and 3B are perspective views showing the flexible substrate on which various components constituting the functioning part are mounted, wherein FIG. 3A is a perspective view of a front surface of the flexible substrate, and FIG. 3B is a perspective view of a rear surface of the flexible substrate.

FIGS. 4A and 4B are diagrams showing a vital information measuring device according to a first embodiment of the invention, wherein FIG. 4A is a front view, and FIG. 4B is a side view.

FIGS. 7A and 7B are diagrams showing a vital information-measuring device according to a second embodiment of the invention, wherein FIG. 7A is a front view, and FIG. 7B is a rear view.

FIGS. 9A and 9B are diagrams showing a vital information measuring device according to a third embodiment of the invention, wherein FIG. 9A is a front view, and FIG. 9B is a rear view.

FIGS. 11A and 11B are diagrams showing a vital information measuring device according to a fourth embodiment of the invention, wherein FIG. 11A is a cross-sectional side view, and FIG. 11B is a top plan view.

FIGS. 13A through 13C are diagrams showing a vital information measuring device according to a fifth embodiment of the invention, wherein FIG. 13A is a front view, FIG. 13B is a rear view, and FIG. 13C is an exploded view.

FIGS. 14A through 14C are diagrams showing a vital information measuring device according to a sixth embodiment of the invention, wherein FIG. 14A is a front view, FIG. 14B is a rear view, and FIG. 14C is a cross-sectional view.

FIGS. 18A through 18C are diagrams showing a vital information measuring device according to a seventh embodiment of the invention, wherein FIG. 18A is a front view, FIG. 18B is a side view, and FIG. 18C is a side view showing a used state of the vital information measuring device.

DETAILED DESCRIPTION OF THE PREFERRED EMBODIMENTS

Figure 3A:
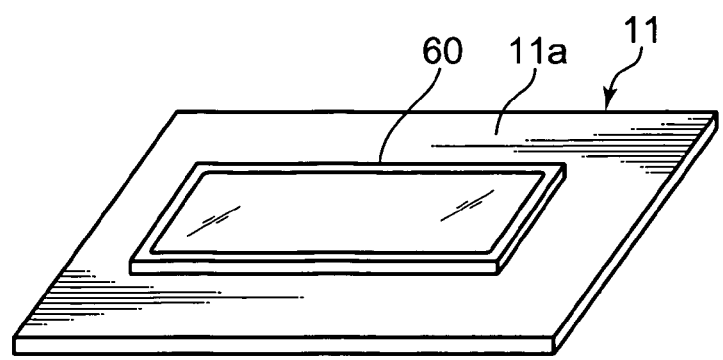

In the following, embodiments of the invention are described referring to the drawings.

Description on Basic Embodiment

FIG. 1 is a plan view briefly showing an arrangement of a vital information measuring device "S" according to an embodiment of the invention. The vital information measuring device "S" includes a flexible substrate 10 mounted with a functioning part "F" thereon, and an outer member 20 for covering the flexible substrate 10. In this embodiment, there are mounted, on the flexible substrate 10, a sensor section 30 for sequentially measuring a parameter relating to certain vital information, a circuit section 40 for performing a predetermined process with respect to a measurement signal outputted from the sensor section 30, a memory section 50 for storing therein the measurement signal or measurement data after the process by the circuit section 40, a display section 60 for displaying thereon certain information relating to the measurement, and a power source section 70 for supplying a drive voltage to the respective sections, which serve as the functioning part "F".

The flexible substrate 10 is a flexible base member constructed in such a manner that a conductive pattern made of copper or a copper alloy is fabricated on a plastic film made of e.g. polyimide or polyester. As mentioned above, the various sections or components constituting the functioning part "F" are mounted on the flexible substrate 10.

The outer member 20 is functioned to protect the flexible substrate 10 from an external force, and is also functioned to waterproof the flexible substrate 10, or to block the flexible substrate 10 from light by providing a member having a waterproof function or a member having a light blocking function for the outer member 20, according to needs. With this arrangement, in the case where it is required to attach the vital information measuring device "S" continuously for a long time for sequential measurements, for instance, a subject is allowed to take a bath or take a shower, while wearing the vital information measuring device "S" by making the outer member 20 waterproof. Also, in the case where the sensor section 30 performs an optical measurement, using an LED or a light detector, blocking the flexible substrate 10 from light by the outer member 20 enables to keep the measuring device from external light which may affect measurement results.

The shape of the outer member 20 is not specifically limited. The outer member 20 may have a sheet-like shape to cover one surface of the flexible substrate 10, or a bag-like shape for accommodating the flexible substrate 10 therein, for instance. The flexible substrate 10 and the outer member 20 may be separated from each other or movable relative to each other. It is desirable to integrally form the flexible substrate 10 with the outer member 20 in order to securely position the sensor section 30 relative to the outer member 20. In this sense, the outer member 20 may be of a sealing or coating type of fixedly sealing the flexible substrate 10 therein. Alternatively, the outer member 20 may be provided with a support structure for integrally and detachably holding the flexible substrate 10 thereon. In the altered arrangement, the flexible substrate 10 can be positioned relative to the outer member 20, using the support structure, and the flexible substrate 10 can be easily detached from the outer member 20, thereby enhancing operability of the vital information measuring device "S".

Preferably, the outer member 20 may be integrally formed with an adhesive layer having an adhesion to a human skin, a locking member for fixedly attaching the outer member 20 to a body part, or a like member in order to easily mount the vital information measuring device "S" to the subject. The flexible substrate 10 and the outer member 20 may have outer configurations depending on the attached site of the vital information measuring device "S" onto the subject, or the arrangement of the sensor section 30. Some examples concerning the outer configurations of the flexible substrate 10 and the outer member 20 will be described later in the section "Description on Various Embodiments Concerning Shapes".

The sensor section 30 is a part for sequentially measuring a certain parameter relating to vital information on the subject. The sensor section 30 includes various sensing elements depending on the kind of vital information to be detected. For measuring blood oxygen saturations i.e. $SpO_2$ or pulse waveforms, for instance, a light emitter such as an LED (in case of $SpO_2$ measurement, a two-wavelength LED is used) and a light detector such as a silicon light detector are provided. In this arrangement, a member having a light blocking function is used as the outer member 20. For measuring body positions/body movements, and chest and abdominal movements of the subject in respiration, an acceleration sensor or the like is provided. For measuring electrocardiographic waveforms, electromyographic waveforms, or the like, electrodes for detecting a cardiac activity potential of the subject are provided. In this case, a member having a waterproof function is used as the outer member 20 to prevent an electric leakage or the like. For measuring air flow rates through mouth or nose, i.e. respiratory movements of the subject, a temperature sensor for detecting a temperature rise resulting from the breathing is provided. For detecting snoring sounds, a compact microphone or the like is provided.

The circuit section 40 performs a predetermined process with respect to a measurement signal concerning vital information, which is outputted from the sensor section 30. The circuit section 40 includes various electronic components, integrated circuit components, a CPU (Central Processing Unit), and the like. The circuit section 40 functionally includes an A/D converter for converting the analog measurement signal outputted from the sensor section 30 into a digital signal, an analysis processor for performing predetermined data analysis with respect to the digital signal, and a controller for controlling the operations of the respective sections of the functioning part "F". The controller further has a function of controlling an operation of measuring vital information by the sensor section 30, an operation of recording the measurement signal or measurement data into the memory section 50 in association with measurement time information, and an operation of displaying, on the display section 60, ongoing measurement status information or information relating to the measured vital information, for instance.

The memory section 50 includes an ROM (Read Only Memory) for storing a control program for the vital information measuring device "S", or the like, an EEPROM (Electrically Erasable Programmable ROM) for temporarily storing data such as a computation process or a control process, and an involatile memory such as a flash memory, so that the measurement signal or the measurement data after the analysis is stored in association with the measurement time information. The association enables to easily perform posterior data analysis, and to correlate the corresponding measurement data with the measurement time in the case where two or more measurement data are detected, for instance, in the case where data for obtaining $SpO_2$ and data for obtaining a pulse waveform are detected from the same sensor section 30.

The display section 60 includes an LED display device provided with one or more LEDs, a flexible liquid crystal display device, or an organic photoluminescence display device. The display section 60 displays the ongoing measurement status information such as information indicating that the device "S" is under measurement, or measurement information as a live indication; or information in association with the measured vital information such as information concerning a measurement data analysis result as lighting/blinking information, textual/numeral/symbol information, picture indication, or character information. The LED display device performs lighting/blinking operations in association with the ongoing measurement status information or the measured vital information. The flexible crystal display device displays, on a liquid crystal display screen, a proper indication in association with the ongoing measurement status information or the measured vital information. A display device having a property that a display color is varied depending on a current capacity or a like device may be used as the display section 60.

The power source section 70 is provided with a power source circuit and a power source battery such a button battery, and supplies a drive voltage to the respective sections of the functioning part "F". Preferably, the power source circuit may have a function of automatic power off (APO). Also, a switch or a like device for allowing a user to start supplying the drive voltage may be provided. Alternatively, an arrangement may be provided, in which a power supply is started in response to mounting the vital information measuring device "S" to the subject's body, or interference of the battery with a part of the subject's body in mounting, or in which a power supply is started by partial breakage of the flexible substrate 10, or removal of a part of the flexible substrate 10, in place of providing the switch. These arrangements will be described later by way of examples.

Alternatively, a power generator for generating an electric power, utilizing heat energy of the subject i.e. a heat power generator may be provided in place of the power source battery. The heat power generator generates an electric power based on Seebeck effect, utilizing a difference in temperature between an area of the heat power generator which is heated by the body temperature of the subject due to a contact with a part of the subject's body, and an area thereof away from the body part. Use of the heat power generator is advantageous, because an electric power is generated, utilizing the body temperature of the subject. This eliminates the need of providing part such as the button battery in the vital information measuring device "S". Also, this arrangement enables to start measurement upon mounting the vital information measuring device "S" to the subject, because body temperature detection, followed by power generation, is started upon mounting the vital information measuring device "S" to the subject.

An exemplified operation of the vital information measuring device "S" having the above arrangement is briefly described. When measurement is started, the sensor section 30 measures vital information at each sampling frequency, and a measurement signal is sequentially outputted from the sensor section 30. After the measurement signal is converted into a digital signal by the circuit section 40, the digital signal is stored in the memory section 50 in association with the measurement time information, using a timer function provided in the circuit section 40. The measurement operation is cyclically repeated for a measurement period, whereby the measurement data are accumulated in the memory section 50. After the measurement is completed, the measurement data stored in the memory section 50 is read out therefrom by the analysis processor provided in the circuit section 40 so as to perform predetermined data analysis useful for finding a disease or the like. The analysis result is displayed on the display section 60 as lighting information or textual/numeral/symbol information, according to needs. The measurement result or the analysis result may be displayed on the display section 60 as a live indication during the measurement period.

With the thus-constructed vital information measuring device "S", there are mounted, on the single flexible substrate 10, the functioning part necessary for vital information measurement, i.e. the sensor section 30, the circuit section 40, the memory section 50, the display section 60, and the power source section 70. This eliminates, unlike the conventional art, the need of a cable for electrically connecting the sensor device to the device main body, or a mechanism for performing radio communication between the sensor device and the device main body. This enables to simplify the arrangement of the vital information measuring device, and to remarkably reduce stress of the subject involved in wearing the vital information measuring device, because the arrangement is free from entangling of the cable.

Description on Embodiment as Pulse Oximeter

In this section, an embodiment of the invention is described by an example of a pulse oximeter for measuring $SpO_2$. Screening on sleep apnea syndrome (SAS) can be performed by measuring a variation in $SpO_2$ in the subject's sleep. It is desirable to suppress stress of the subject as much as possible, in light of the fact that the subject has to wear the pulse oximeter overnight. In view of this, the pulse oximeter is a preferred embodiment of the vital information measuring device of the invention which is suitable for a long time wearing.

Description on Electrical Configuration

FIG. 2 is a block diagram showing an electrical configuration of a functioning part to be mounted on a flexible substrate 11 in the case where the inventive vital information measuring device is produced as a pulse oximeter. The flexible substrate 11 includes, as the functioning part, a sensor section 30 having a light emitter 31 and a light detector 32, a measurement circuit section 41 and a main controller 42 corresponding to the circuit section 40 in FIG. 1, a memory section 50 equivalent to the memory section 50 in FIG. 1, a display section 60 equivalent to the display section 60 in FIG. 1, a power source section 70 equivalent to the power source section 70 in FIG. 1, a communication section 80 for performing data communication with another electrical apparatus, and an operation section 90 for allowing a user to enter certain operation information. Description on the memory section 50, the display section 60, and the power source section 70 is omitted herein. The communication section 80 and the operation section 90 may not be mounted on the flexible substrate 11.

The light emitter 31 of the sensor section 30 is composed of LEDs for generating light of two wavelengths $\lambda 1$ and $\lambda 2$ different from each other, for instance, a red LED for generating red light of the wavelength $\lambda 1$ in a red color region, and an infrared LED for generating infrared light of the wavelength $\lambda 2$ in an infrared region. The light detector 32 includes a photoelectric conversion device for receiving the light from the light emitter 31 to generate a current commensurate with the intensity of the received light. An example of the photoelectric conversion device is a light detecting device such as a silicon photodiode having photosensitivity to at least the light of the wavelengths $\lambda 1$ and $\lambda 2$.

The light emitter 31 and the light detector 32 may be disposed opposite to each other so that a living tissue e.g. a fingertip of the subject for which $SpO_2$ is to be measured is securely held therebetween so as to detect the light transmitted through the living body, or may be disposed adjacent to each other to detect the light reflected from the living body. With this arrangement, the light of the wavelength $\lambda 1$ and the light of the wavelength $\lambda 2$ emitted from the light emitter 31 are detected by the light detector 32 through the living body.

The measurement circuit section 41 has an emission controller 411 connected to the light emitter 31, and an A/D converter 412 connected to the light detector 32. The emission controller 411 controls the light emitter 31 to alternately emit red LED light and infrared LED light based on an emission control signal outputted from the measurement controller 421 of the main controller 42 to be described later with a predetermined sampling frequency. With this arrangement, the red light of the wavelength $\lambda 1$ and the infrared light of the wavelength $\lambda 2$ are alternately emitted. The measurement controller 421 controls the A/D converter 412 to acquire a photoelectric conversion signal i.e. a measurement signal outputted from the light detector 32 in synchronism with the light emission from the light emitter 31, and to convert the acquired measurement signal into a digital signal for outputting the digital signal to the main controller 42.

Oxygen is transported by oxidation/reduction of hemoglobin in the blood. The hemoglobin has such optical characteristics that absorption of red light of the wavelength $\lambda 1$ is decreased, and absorption of infrared light of the wavelength $\lambda 2$ is increased when the hemoglobin is oxidized, and, conversely, absorption of red light of the wavelength $\lambda 1$ is increased and absorption of infrared light of the wavelength $\lambda 2$ is decreased when the hemoglobin is reduced. The sensor section 30 is designed to utilize the optical characteristics. It is possible to obtain the $SpO_2$ by measuring a variation in transmitted amounts of the red light of the wavelength $\lambda 1$ and the infrared light of the wavelength $\lambda 2$, which are detected by the light detector 32.

The main controller 42 has a CPU. The main controller 42 is adapted to control operations of the respective sections mounted on the flexible substrate 11, and is functionally provided with the measurement controller 421, a recording controller 422, a display controller 423, and an analysis processor 424. The measurement controller 421 controls the sensor section 30 to measure vital information based on a predetermined measurement program. Specifically, the measurement controller 421 issues a timing pulse or the like to the emission controller 411 and to the A/D converter 412, controls the light emitter 31 to emit light at each sampling frequency, and controls the light detector 32 to acquire a photo-electric conversion signal i.e. a measurement signal in synchronism with the emission timing.

The recording controller 422 controllably records the digital measurement signal outputted from the A/D converter 412, or measurement data after a certain data analysis by the analysis processor 424 into the memory section 50 in association with the measurement time information, using the timer function or a like function provided in the CPU.

The display controller 423 controllably displays, on the display section 60, ongoing measurement status information concerning the $SpO_2$, or an analysis result obtained by analyzing the measured $SpO_2$ information by the analysis processor 424 e.g. a degree of variation of $SpO_2$ during the subject's sleep in a predetermined display format.

The analysis processor 424 performs a predetermined data analysis based on the measurement signal acquired by the sensor section 30. For instance, in case of performing data analysis for screening SAS, the analysis processor 424 generates time-based data i.e. an $SpO_2$ curve during a measurement period i.e. a sleep period by reading $SpO_2$ values recorded in the memory section 50, and detects the number of appearance of a portion of the $SpO_2$ curve where the $SpO_2$ values have temporarily dropped i.e. a lowest peak of the $SpO_2$ values, which represents that a respiratory failure appears in the subject, a degree of lowering of the $SpO_2$ values i.e. a blood oxygen saturation lowering index, or the like, according to computation.

The communication section 80 includes an interface device for enabling data communication in the case where the data recorded in the memory section 50 is to be transferred to the another electrical apparatus such as a personal computer. The operation section 90 includes operation buttons through which the user is allowed to designate a measurement start or to enter various operation command information to the main controller 42.

An operation of the flexible substrate 11 having the above arrangement is briefly described as follows. When a measurement is started, the measurement controller 421 controls the sensor section 30 to operate so that a measurement signal in accordance with transmitted light or reflected light is outputted from the sensor section 30 at each sampling frequency. The measurement signal is converted into a digital signal by the A/D converter 412, and then, the digital signal is stored in the memory section 50 as an $SpO_2$ value at each measurement time by the recording controller 422. The measurement operation is cyclically repeated during a measurement period, and the $SpO_2$ values at the respective measurement periods are accumulated in the memory section 50. After the measurement is completed, in case of screening SAS, for instance, the analysis processor 424 reads out the $SpO_2$ values from the memory section 50, and creates an $SpO_2$ curve by developing the $SpO_2$ values along a time axis. Then, the analysis processor 424 obtains information relating to a screening result on SAS based on the number of times of appearance of the $SpO_2$ lowest peak in the $SpO_2$ curve, a degree of lowering of the $SpO_2$ values in the lowest peaks, or the like. The analysis result information is displayed on the display section 60 by the display controller 423 in an appropriate display format.

As described above, combining the flexible substrate usable as the pulse oximeter with a proper outer member enables to provide a preferred embodiment of the inventive vital information measuring device. The flexible substrate and the outer member may be formed into various shapes, considering fittability of the vital information measuring device to the subject's body, or viewability of the display section. The following section describes various embodiments concerning the shapes of the flexible substrate and the outer member, including mounting manners as to how the functioning part is mounted on the flexible substrate.

Description on Various Embodiments Concerning Shapes

Figure 3B:
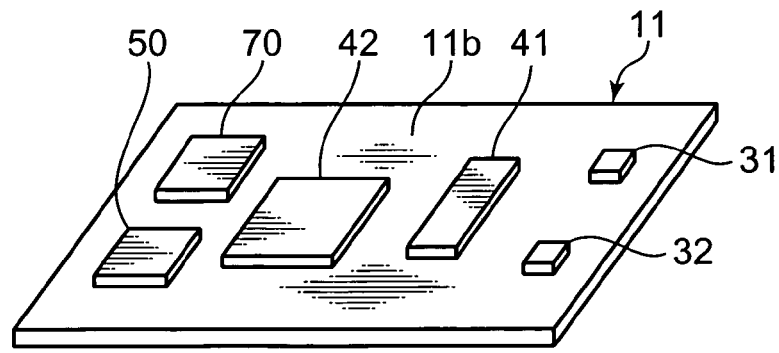

First, a preferred embodiment concerning a manner of mounting a functioning part on a flexible substrate is described. FIGS. 3A and 3B are perspective views showing the flexible substrate 11 mounted with the components constituting the functioning part. As shown in FIG. 3A, a transversely long display section 60 is mounted on one surface i.e. a front surface 11a of the flexible substrate 11. As shown in FIG. 3B, a light emitter 31, a light detector 32, a measurement circuit controller 41, a main controller 42, a memory section 50, and a power source section 70 are mounted on the other surface, i.e. a rear surface 11b of the flexible substrate 11.

In the flexible substrate 11, the front surface 11a serves as a viewing surface, and the rear surface 11b serves as a measurement surface where light is projected and detected by the light emitter 31 and the light detector 32, respectively. With this arrangement, contacting the rear surface 11b with a predetermined subject's body surface site e.g. a fingertip of the subject enables to measure vital information of the subject, while allowing a user including the subject to view the display section 60. Since the display section 60 is arranged on the front surface 11a of the flexible substrate 11, a large area can be secured for the display section 60. Furthermore, since the both surfaces of the flexible substrate 11 can be utilized, the size of the flexible substrate 11 can be decreased. A part of the components to be mounted on the rear surface 11b of the flexible substrate 11 except for the light emitter 31 and the light detector 32 may be mounted on the front surface 11a of the flexible substrate 11.

FIGS. 4A and 4B are diagrams showing a vital information measuring device "S1", using the flexible substrate 11, according to a first embodiment of the invention. FIG. 4A is a front view, and FIG. 4B is a side view. The vital information measuring device "S1" includes the flexible substrate 11, and an outer member 21 which is so designed as to cover the front surface 11a of the flexible substrate 11.

The outer member 21 has a flexibility, is made of a resin material or a like material having a light blocking function and a waterproof function, and is formed into a sheet-like shape, with a vertical size in FIGS. 4A and 4B sufficiently larger than the corresponding size of the flexible substrate 11. The vertically long sheet-like shape is advantageous in winding the outer member 21 around a fingertip, like an adhesive tape (see FIG. 6). An adhesive layer 21A having an adhesion to a human skin is formed on one surface of the outer member 21. A window portion 21T is formed near a central part of the outer member 21. The window portion 21T is defined so that the user can view the display screen of the display section 60 through the window portion 21T. The window portion 21T is defined by cutting an area corresponding to the window portion 21T, or by forming a transparent resin layer with an area corresponding to the window portion 21T being removed, which is obtained, for instance, by placing, onto a transparent sheet, a non-translucent sheet with an area corresponding to the window portion 21T being cutout.

The flexible substrate 11 is integrally formed with the outer member 21 in such a manner that the front surface 11a (see FIG. 3A) of the flexible substrate 11 is opposed to the adhesive layer 21A of the outer member 21. The flexible substrate 11 and the outer member 21 are made integral, with the display section 60 mounted on the front surface 11a being positioned relative to the window portion 21T, whereby the user is allowed to observe the display screen of the display section 60 through the window portion 21T. The flexible substrate 11 may be integrally formed with the outer member 21, utilizing the adhesion of the adhesive layer 21A, or may be integrally formed with the outer member 21 by way of an additional adhesive layer to secure more adhesiveness. Further alternatively, the flexible substrate 11 and the outer member 21 may be individual members substantially with no adhesion or bonding.

Figure 6:
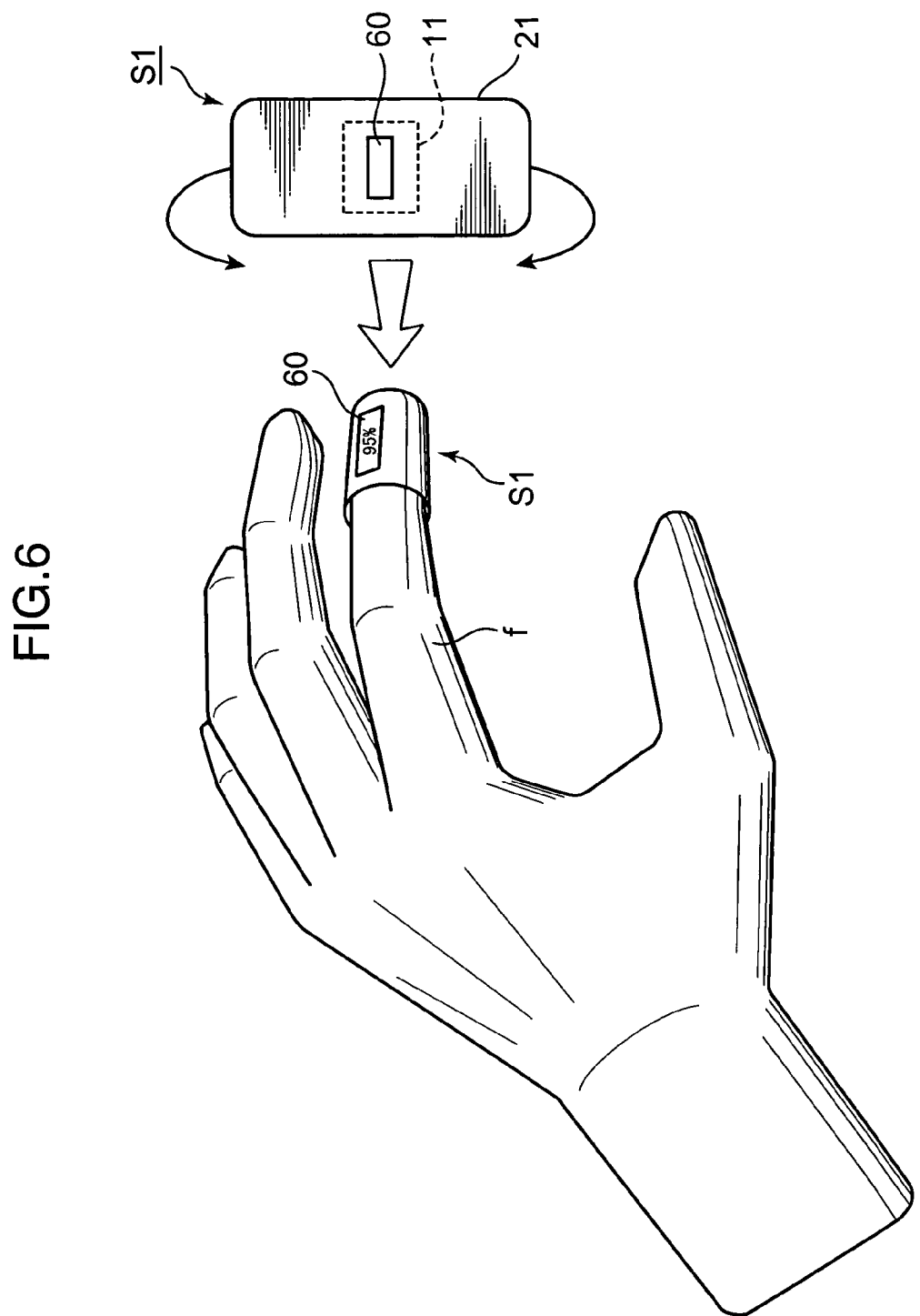
FIG. 6 is a perspective view showing how the vital information measuring device in the first embodiment is removably attached to a fingertip of a subject for measurement.

The vital information measuring device "S1" having the above arrangement is, as shown in FIG. 6, removably attached to a subject's body portion by winding longitudinal both ends of the outer member 21 around a fingertip of the finger "f" of the subject to be measured, i.e., a fingertip of the subject. While the vital information measuring device "S1" is being mounted, the flexible substrate 11 is flexibly deformed along the configuration of the fingertip, and the light emitter 31 and the light detector 32 are brought into contact with the fingertip. The adhesive layer 21A is adhesively attached to the surface of the fingertip, and is also adhesively attached to a part of the front surface of the outer member 21.

Figure 5A:
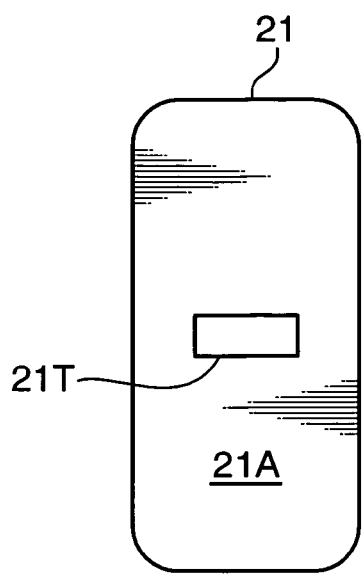
FIGS. 5A through 5C are explanatory diagrams for describing a setting direction of a display section.
Figure 5B:
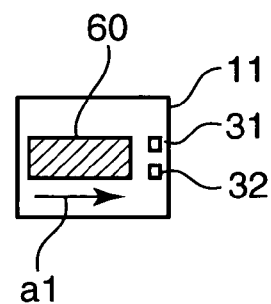
Figure 5C:
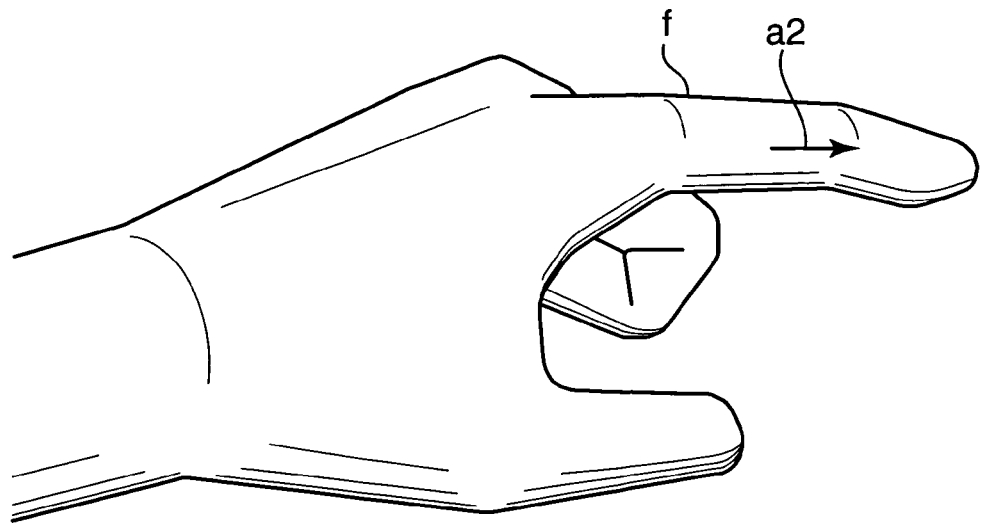

In the attachment, the longitudinal direction of the window portion 21T of the outer member 21 and the display section 60 is made substantially coincident with the extending direction of the finger "f", in light of the point that the transversely long display section 60 is mounted on the flexible substrate 11. Specifically, as shown in FIGS. 5A through 5C, it is desirable to locate the flexible substrate 11 onto the finger "f" to be measured in such a manner as to substantially make the direction of the arrow "a2" in FIG. 5C indicating the extending direction of the finger "f" substantially coincident with the direction of the arrow "a1" indicating the longitudinal direction of the display section 60 for securing flatness of the display screen of the display section 60 to enhance viewability. For this purpose, the flexible substrate 11 is mounted on the outer member 21 so as to make the extending direction i.e. the arrow direction "a1" of the display section 60 substantially coincident with the extending direction i.e. the arrow direction "a2" of the finger "f" to be measured in a state that the outer member 21 is removably attached to the fingertip. In other words, the flexible substrate 11 is mounted on the outer member 21 in such a manner as to make the longitudinal direction of the window portion 21T substantially coincident with the extending direction of the finger "f" to be measured in removably attaching the outer member 21 to the fingertip. With this arrangement, as shown in FIG. 6, viewability of the display screen of the display section 60 is enhanced. Particularly, displaying an indication in the longitudinal direction of the flexible substrate 11 enables to further enhance viewability from a user's view. In FIG. 6, a numerical value "95%" is displayed along the longitudinal direction of the flexible substrate 11.

Figure 8:
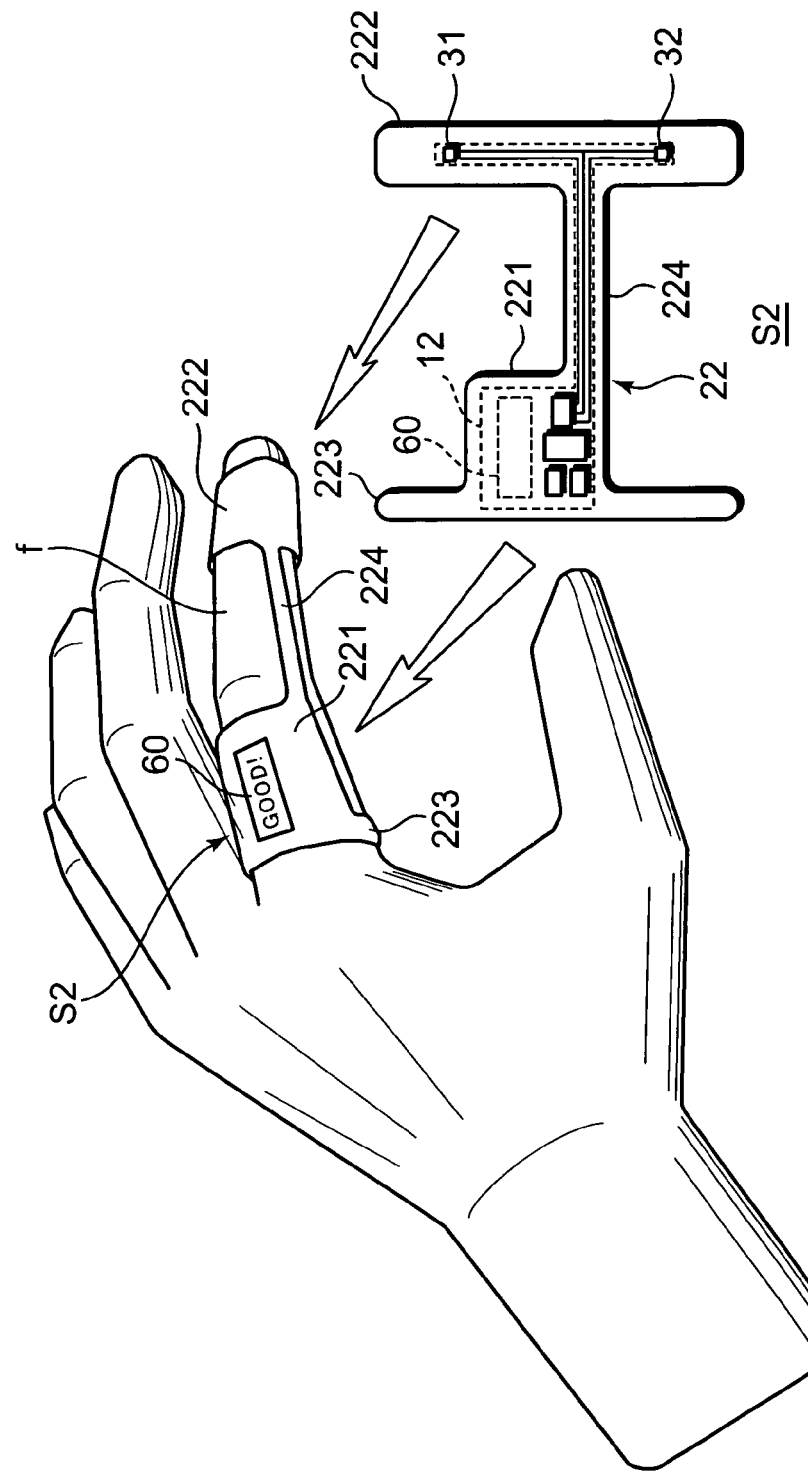
FIG. 8 is a perspective view showing how the vital information measuring device in the second embodiment is removably attached to the fingertip of the subject.

FIGS. 7A and 7B are diagrams showing a vital information measuring device "S2" according to a second embodiment of the invention, wherein FIG. 7A is a front view, and FIG. 7B is a rear view. FIG. 8 is a perspective view showing how the vital information measuring device "S2" is mounted on the finger "f" to be measured. The vital information measuring device "S2" is similar to the vital information measuring device "S1" in the first embodiment in that the vital information measuring device "S2" includes a flexible substrate 12, and an outer member 22 which is so designed as to cover one surface of the flexible substrate 12, except that the vital information measuring device "S2" has an improved configuration capable of enhancing stability and fittability in removably attaching the vital information measuring device "S2" to the finger "f" to be measured.

The flexible substrate 12 includes a rectangular main portion 121, an oblong probe portion 122, and an oblong connecting portion 123. A display section 60 is mounted on a front surface of the main portion 121, and a measurement circuit section 41, a main controller 42, a memory section 50, and a power source section 70 are mounted on a rear surface of the main portion 121. A light emitter 31 and a light detector 32 are mounted on the probe portion 122. The connecting portion 123 is adapted to integrally connecting the main portion 121 to the probe portion 122. As shown in FIG. 7A, the probe portion 122 and the connecting portion 123 extend orthogonal to each other, and are integrally formed into a substantially T-shape. In the second embodiment, the light emitter 31 and the light detector 32 are disposed away from each other, whereby an optical system for transmitting light through a fingertip for measurement is established.

The outer member 22 includes a rectangular portion 221, a first band portion 222, a second band portion 223, and a third band portion 224. The rectangular portion 221 is adapted to cover the main portion 121 of the flexible substrate 12. The first band portion 222 is adapted to cover the probe portion 122, and also serves as a locking member for fixedly mounting the probe portion 122 onto a distal end of the finger "f" to be measured. The second band portion 223 extends from an end portion of the rectangular portion 221, and serves as a locking member for fixedly mounting the main portion 121 onto a base end of the finger "f" to be measured. The third band portion 224 is adapted to connect the rectangular portion 221 to the first band portion 222 while covering the connecting portion 123.

A window portion 22T is formed in the rectangular portion 221 of the outer member 22, so that the user can view the display section 60 mounted on the flexible substrate 12 through the window portion 22T. Both ends of the first band portion 222 constitute a first winding portion 222a and a second winding portion 222b to be wound around the distal end of the finger "f" to be measured, respectively. An adhesive layer 222c is formed on the first winding portion 222a. Similarly to the first band portion 222, both ends of the second band portion 223 constitute a first winding portion 223a and a second winding portion 223b to be wound around the base end of the finger "f" to be measured, respectively. An adhesive layer 223c is formed on the first winding portion 223a.

The vital information measuring device "S2" having the above construction is, as shown in FIG. 8, removably attached to the finger "f" to be measured, using the first band portion 222 and the second band portion 223. Specifically, winding the first band portion 222 around the distal end of the finger "f" to be measured allows the probe portion 122 of the flexible substrate 12 to be mounted on the finger "f" to be measured so that the light emitter 31 and the light detector 32 are brought into contact with the distal end of the finger "f" to be measured. In the attachment, the second winding portion 222b is placed over the adhesive layer 222c of the first winding portion 222a to thereby make the vital information measuring device "S2" unmovable relative to the finger "f". Also, winding the second band portion 223 around the base end of the finger "f" to be measured allows the main portion 121 carrying the display section 60 to be mounted on the finger "f" so that the display section 60 is exposed outside. In the attachment, the second winding portion 223b is placed over the adhesive layer 223c of the first winding portion 223a to thereby make the vital information measuring device "S2" unmovable relative to the finger "f".

With the vital information measuring device "S2" having the above construction, the vital information measuring device "S2" is made unmovable relative to the finger "f" to be measured at the two sites i.e. the distal end and the base end of the finger "f" to be measured by the first band portion 222 and the second band portion 223, thereby enhancing stability in mounting. Also, as shown in FIG. 8, setting the length of the third band portion 224 to such a length as to expose the first joint and the second joint of the finger "f" to be measured secures desirable fittability without obstructing a flexing action of the finger "f".

Figure 10:
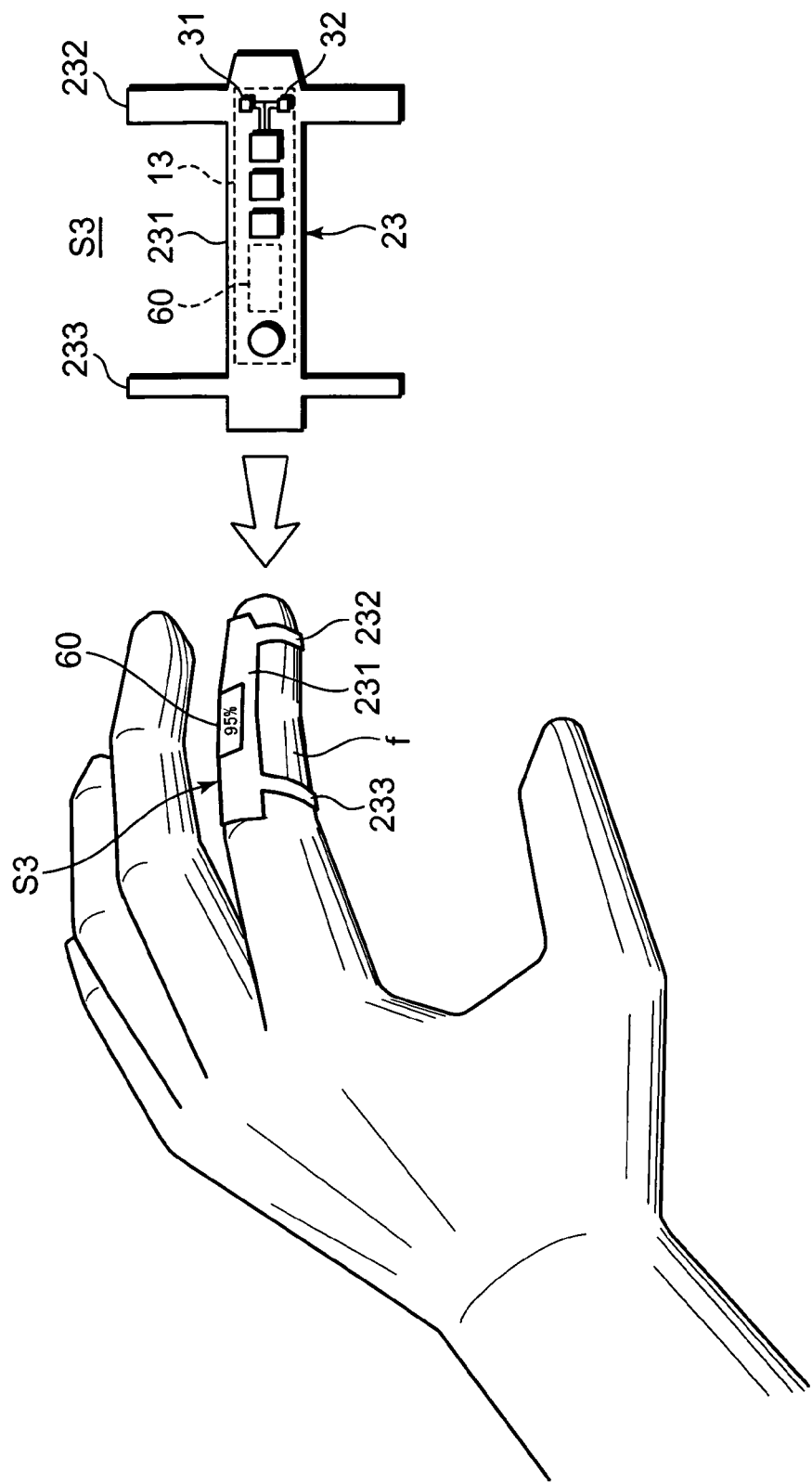
FIG. 10 is a perspective view showing how the vital information measuring device in the third embodiment is removably attached to the fingertip of the subject.

FIGS. 9A and 9B are diagrams showing a vital information measuring device "S3" according to a third embodiment of the invention, wherein FIG. 9A is a front view, and FIG. 9B is a rear view. FIG. 10 is a perspective view showing how the vital information measuring device "S3" is removably attached to the finger "f" to be measured. The vital information measuring device "S3" is similar to the vital information measuring device "S2" in the second embodiment in that the vital information measuring device "S3" includes a flexible substrate 13, and an outer member 23 which is so designed as to cover one surface of the flexible substrate 13, and that the vital information measuring device "S3" has two locking members, except that the vital information measuring device "S3" has a more simplified configuration concerning the flexible substrate 13 and the outer member 23.

In the third embodiment, the flexible substrate 13 has an oblong shape, with a width thereof smaller than the width of a finger. A display section 60 is mounted on a front surface of the flexible substrate 13, and a light emitter 31, a light detector 32, a measurement circuit section 41, a main controller 42, a memory section 50, and a power source section 70 are linearly mounted on a rear surface of the flexible substrate 13. In the third embodiment, the light emitter 31 and the light detector 32 are arranged in proximity and juxtaposed to each other, opposing a back portion or a ball portion of the fingertip, whereby an optical system for irradiating light to be measured and receiving reflected light is established.

The outer member 23 includes a rectangular portion 231 for covering the flexible substrate 13, and a first band portion 232 and a second band portion 233 which extend from longitudinal both ends of the rectangular portion 231, respectively. A window portion 23T is formed in the rectangular portion 231 of the outer member 23 so that the user can view the display section 60 mounted on the flexible substrate 13 through the window portion 23T. The first band portion 232 and the second band portion 233 serve as locking members for fixedly attaching the vital information measuring device "S3" to the finger "f" to be measured. Specifically, both ends of the first band portion 232 constitute a first winding portion 232a and a second winding portion 232b to be wound around a portion near a tip end of the finger "f" to be measured. Both ends of the second band portion 233 constitute a first winding portion 233a and a second winding portion 233b to be wound around an intermediate portion of the finger "f" to be measured. The first winding portion 232a is formed with an adhesive layer 232c, and the first winding portion 233a is formed with an adhesive layer 233c, respectively.

With the vital information measuring device "S3" having the above construction, as shown in FIG. 10, the vital information measuring device "S3" is removably attached to the finger "f" to be measured, with the longitudinal direction thereof being aligned with the extending direction of the finger "f" to be measured, using the first band portion 232 and the second band portion 233. Specifically, the vital information measuring device "S3" is removably attached to the finger "f" to be measured by mounting the rectangular portion 231 near the tip end of the finger "f" to be measured, with the longitudinal direction of the rectangular portion 231 being substantially coincident with the extending direction of the finger "f" to be measured, and by winding the first winding portion 232 and the second winding portion 233 around the respective corresponding sites of the finger "f" to be measured. In the attachment, placing the second winding portion 232b and the second winding portion 233b over the adhesive layer 232c of the first winding portion 232a and over the adhesive layer 233c of the first winding portion 233a respectively allows the vital information measuring device "S3" to be unmovable relative to the finger "f" to be measured. Also, the attachment allows the light emitter 31 and the light detector 32 to be brought into contact with the fingertip, in the example of FIG. 10, the back portion of the fingertip.

With the vital information measuring device "S3" having the above construction, the vital information measuring device "S3" is made unmovable relative to the finger "f" to be measured at the two sites by the first band portion 232 and the second band portion 233. This arrangement enables to enhance stability in mounting the vital information measuring device "S3" onto the finger "f" to be measured, and yet simplify the configuration of the flexible substrate 13 and the outer member 23, thereby reducing a production cost.

Figure 11A:
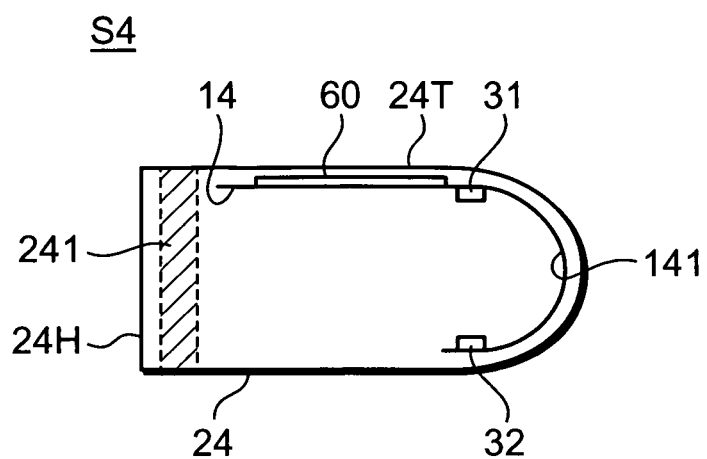
Figure 11B:
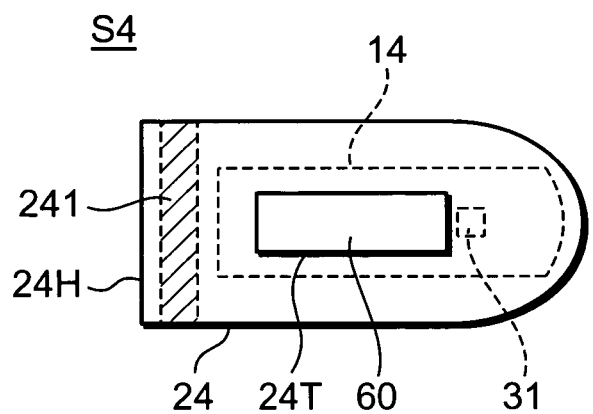
Figure 12:
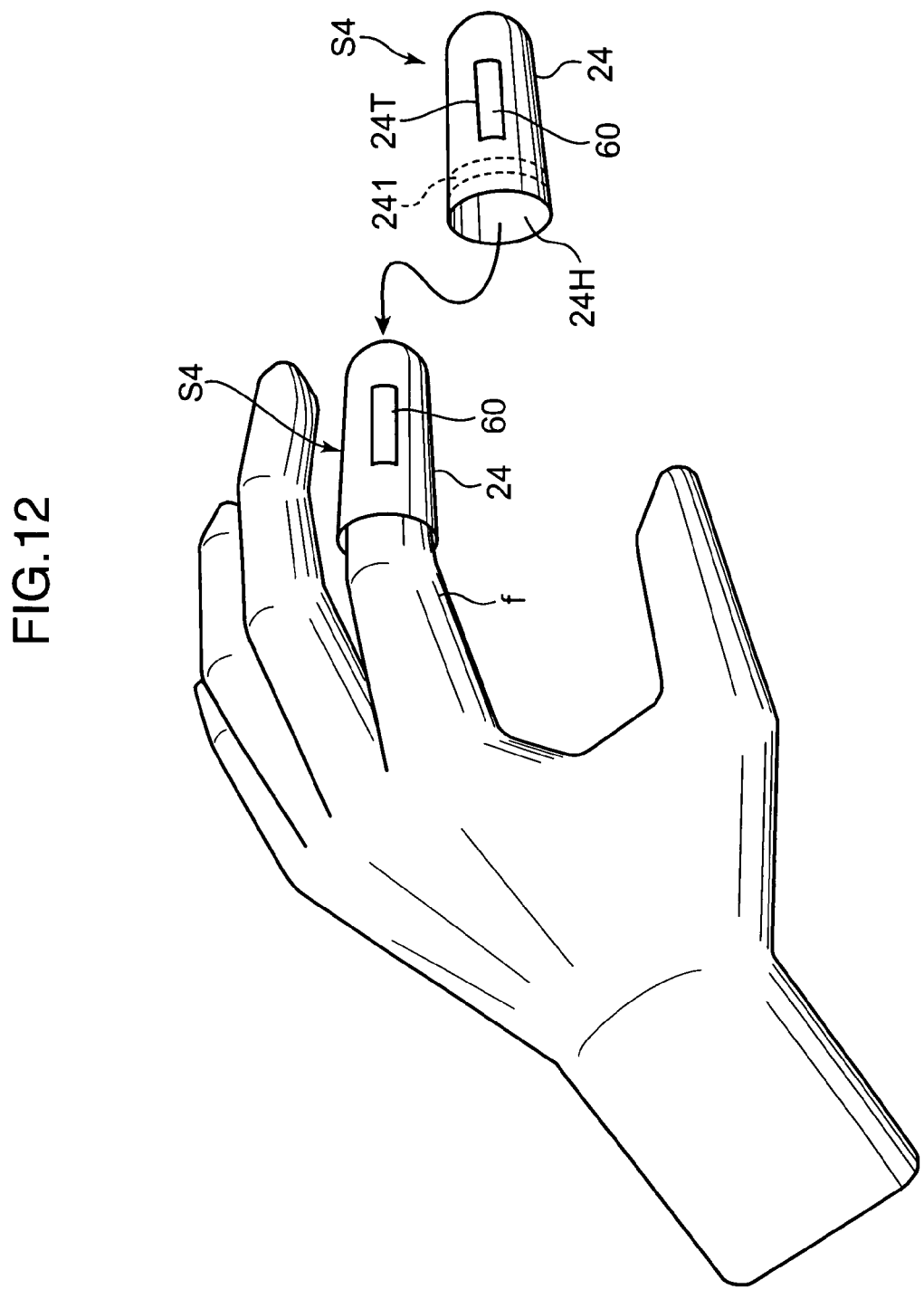
FIG. 12 is a perspective view showing how the vital information measuring device in the fourth embodiment is removably attached to the fingertip of the subject.

FIGS. 11A and 11B are diagrams showing a vital information measuring device "S4" according to a fourth embodiment of the invention, wherein FIG. 11A is a cross-sectional view, and FIG. 11B is a top plan view. FIG. 12 is a perspective view showing how the vital information measuring device "S4" is removably attached to the finger "f" to be measured. The vital information measuring device "S4" includes a rectangular flexible substrate 14, and a fingerstall-like outer member 24 for housing the flexible substrate 14 therein.

As shown in FIGS. 11A and 11B, as in the case of the third embodiment, the flexible substrate 14 has a simplified construction, with a width thereof smaller than the width of a finger. A display section 60 is mounted on a front surface of the flexible substrate 14. A light emitter 31, a light detector 32, and other sections (not shown) constituting the functioning part are mounted on a rear surface of the flexible substrate 14. The light emitter 31 and the light detector 32 are disposed away from each other. As shown in FIG. 11A, the flexible substrate 14 is housed in the outer member 24 in a state that a curved portion 141 is formed between the light emitter 31 and the light detector 32, with extending directions thereof substantially being opposite to each other between the light emitter 31 and the light detector 32. Forming the curved portion 141 enables to dispose the light emitter 31 and the light detector 32 opposite to each other, for instance, the light emitter 31 on a back portion of a fingertip and the light detector 32 on a ball portion of the fingertip in removably attaching the vital information measuring device "S4" to the fingertip, whereby an optical system for irradiating light to be measured and receiving transmitted light is established.

The outer member 24 has a bottomed tubular shape, with an inner diameter capable of fittingly receiving a distal end of the finger "f" to be measured therein. A window portion 24T is formed in a circumferential wall of the outer member 24 so that the user can view, through the window portion 24T, the display screen of the display section 60 mounted on the flexible substrate 14 which is housed in the outer member 24. Also, an annular adhesive layer 241 having an adhesion to a human skin is formed on an inner circumferential wall of the bottomed tubular shaped outer member 24 near an opening 24H thereof.

With the vital information measuring device "S4" having the above construction, as shown in FIG. 12, the vital information measuring device "S4" is removably attached to a distal end of the finger "f" to be measured i.e. the fingertip by fittingly receiving the fingertip through the opening 24H of the outer member 24. After the attachment, adhesively attaching the adhesive layer 241 to the skin near the fingertip allows the vital information measuring device "S4" to be removably attached to the fingertip. Alternatively, the outer member 24 may have an elastic layer having such elasticity as to supply a proper fastening force to the fingertip, in place of the adhesive layer 241. The altered arrangement is advantageous in easily attaching the vital information measuring device "S4" to the fingertip.

Figure 13A:
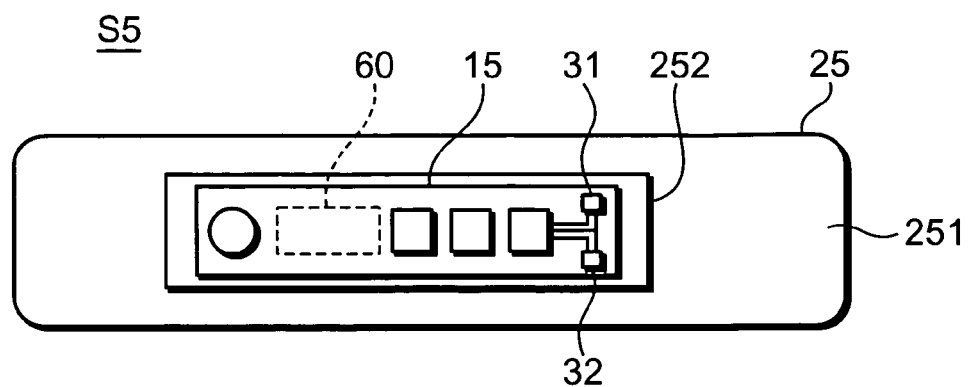
Figure 13B:
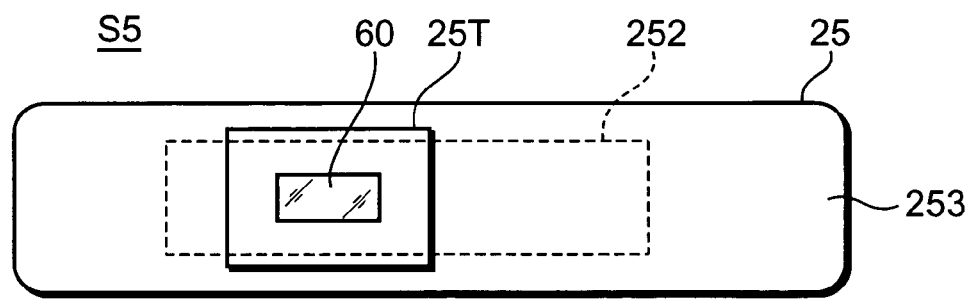
Figure 13C:
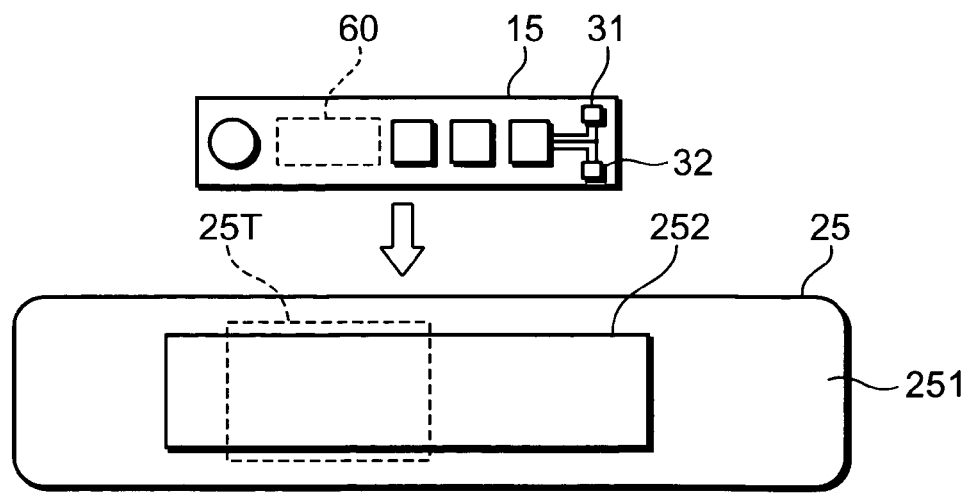

FIGS. 13A through 13C are diagrams showing a vital information measuring device "S5" according to a fifth embodiment of the invention, wherein FIG. 13A is a front view, FIG. 13B is a rear view, and FIG. 13C is an exploded view. The vital information measuring device "S5" includes an oblong flexible substrate 15 and an outer member 25, wherein both surfaces of the flexible substrate 15 are covered by the outer member 25, and the flexible substrate 15 is detachably mounted to the outer member 25.

Similarly to the flexible substrate 13 shown in the third embodiment, a display section 60 is mounted on a front surface of the flexible substrate 15, and various sections of a functioning part including a measurement circuit section are linearly mounted on a rear surface of the flexible substrate 15.

As shown in FIG. 13A, the outer member 25 has, on a rear surface 251 thereof, a transparent pocket member 252, which serves as a detachable support structure and is capable of housing the flexible substrate 15. As shown in FIG. 13B, the outer member 25 is formed, on a front surface 253 thereof, a window portion 25T through which the user is allowed to view the display section 60 of the flexible substrate 15. The outer member 25 has such a length as to be wound around a distal end of the finger "f" to be measured by about 1.5 times, and is formed with a hook-and-loop fastener layer on the rear surface 251 thereof.

As shown in FIG. 13C, the flexible substrate 15 is detachably attached to the transparent pocket member 252. The flexible substrate 15 is integrally held relative to the outer member 25 by housing the flexible substrate 15 in the transparent pocket member 252. The flexible substrate 15 is housed in the transparent pocket member 252 in such a way that the user can view, through the transparent pocket member 252, the surface of the flexible substrate 15 where the light emitter 31 and the light detector 32 are mounted, and that the display section 60 is aligned with the window portion 25T. With this arrangement, light projecting and receiving operations by the light emitter 31 and the light detector 32 are executed smoothly through the transparent pocket member 252, and the user is allowed to view the display screen of the display section 60 through the window portion 25T.

With the vital information measuring device "S5" having the above construction, the vital information measuring device "S5" is removably attached to the finger "f" to be measured by winding the rear surface 251 of the outer member 25, which carries the hook-and-loop fastener layer, around the fingertip, and by engaging both ends of the hook-and-loop fastener layer with each other. The vital information measuring device "S5" is capable of not only being easily attached to the subject but also reusing the outer member 25 by replacing the flexible substrate 15 with a new one, thereby providing the vital information measuring device with superior recyclability.

Figure 14A:
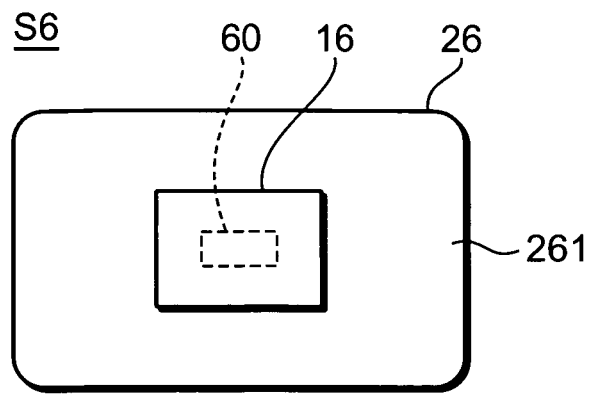
Figure 14B:
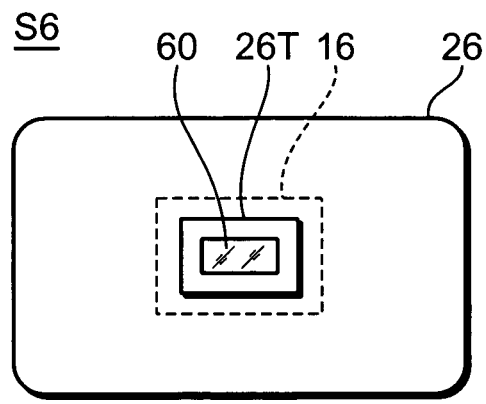
Figure 14C:
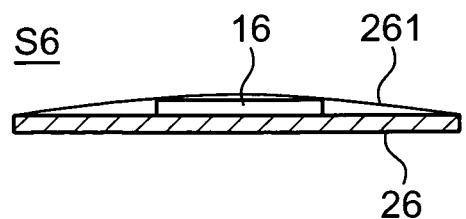

FIGS. 14A through 14C are diagrams showing a vital information measuring device "S6" according to a sixth embodiment of the invention, wherein FIG. 14A is a front view, FIG. 14B is a rear view, and FIG. 14C is a cross-sectional side view. The vital information measuring device "S6" is an embodiment which is adapted to be removably attached to the chest or abdomen of the subject where body movements are relatively large due to respiratory operations or the like, in place of being attached to a fingertip.

The vital information measuring device "S6" includes an approximately square-shaped flexible substrate 16, and an outer member 26. The flexible substrate 16 is provided near a central part on the rear surface of the outer member 26. A window portion 26T is formed in the outer member 26 so that the user can view the display screen of a display section 60 mounted on the flexible substrate 16 through the window portion 26T.

As shown in FIGS. 14A and 14C, the entirety of a rear surface of the flexible substrate 16 corresponding to the side where a light emitter and a light detector are mounted is covered by a transparent adhesive sheet layer 261. In other words, the flexible substrate 16 is sealably closed by the outer member 26 and the adhesive sheet layer 261. With the vital information measuring device "S6" having the above construction, the vital information measuring device "S6" can be securely and planarly adhered to an intended body surface portion of the subject by the adhesive sheet layer 261, which causes no or less displacement or detachment of the vital information measuring device "S6" even if the vital information measuring device "S6" is attached to the chest or abdomen where body movements are relatively large.

Description on Embodiments of Display Section

Figure 15A:
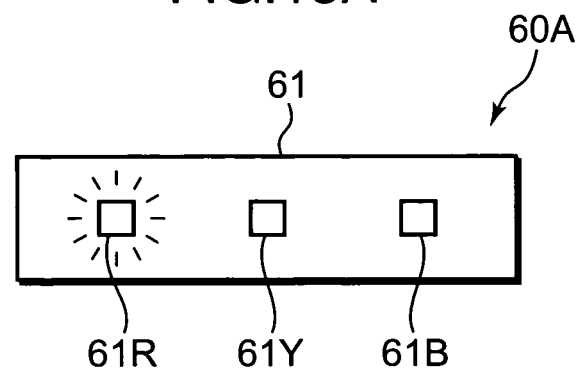
FIGS. 15A and 15B are plan views respectively showing an LED display device using plural LEDs, and a liquid crystal display device using a flexible liquid crystal display.
Figure 15B:
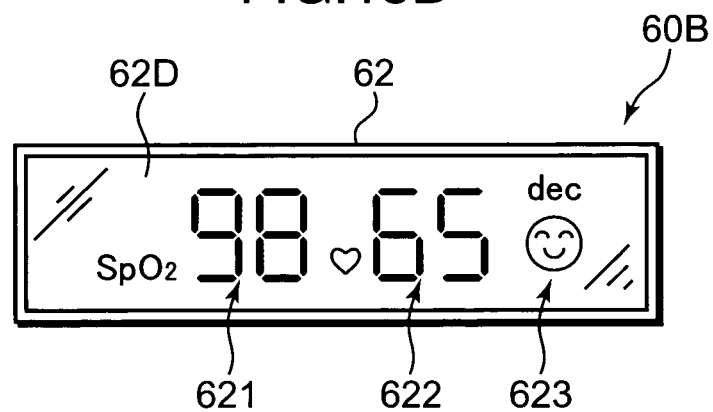

In this section, embodiments of the display section are described. FIGS. 15A and 15B are diagrams showing embodiments of the display section 60. FIG. 15A is a plan view showing an LED display device 60A using plural LEDs, and FIG. 15B is a plan view showing a liquid crystal display device 60B using a flexible liquid crystal display.

The LED display device 60A illustrated in FIG. 15A includes a display substrate 61, and three different LEDs of emitting light of different wavelengths, i.e. a red LED 61R, a yellow LED 61Y, and a blue LED 61B, which are mounted on the display substrate 61. The LED display device 60A enables to perform various indications by allowing the respective LEDs 61R, 61Y, and 61B to perform lighting/blinking operations. For instance, lighting of the blue LED 61B indicates "NORMAL", lighting of the yellow LED 61Y indicates "NEED CARE", and lighting of the red LED 61R indicates "COMPLETE EXAMINATION REQUIRED" in accordance with an analysis result on measurement data by the analysis processor 424 (see FIG. 2). Thus, the indication in association with the measured $SpO_2$ values is displayable.

Alternatively, the LED display device 60A may display an indication representing a measurement status. For instance, if the sensor section 30 is detached from the fingertip during a measurement, the output from the A/D converter 412 shows an obviously abnormal value, as compared with an output based on light transmitted through the living body, or light reflected from the living body. As an arrangement, the controller 42 may detect the abnormality, control the blue LED 61B to emit light while a normal measurement is conducted, and control the red LED 61R to emit light when abnormality has occurred. This arrangement allows the user to confirm whether a normal measurement is conducted at a glance.

The liquid crystal display device 60B illustrated in FIG. 15B includes a display substrate 62, and a liquid display screen 62D mounted on the display substrate 62. An analysis result on the aforementioned measurement data, or information indicating a measurement status, or a live indication concerning the measurement result are displayable on the liquid crystal display screen 62D in terms of appropriate texts, numerals, figures, picture symbols, characters including face marks, or the like. FIG. 15B shows an example, wherein the liquid crystal display screen 62D has an $SpO_2$ indication area 621 for display an $SpO_2$ value, a pulse rate indication area 622 for displaying a pulse rate, and a judgment indication area 623 for displaying a judgment result as to whether the $SpO_2$ value and the pulse rate show normal values in a simplified manner in terms of an expression of a face mark. In the case where a screening result on SAS is displayed on the liquid crystal display screen 62D, for instance, a score, a symbol such as ○ or X, a ranking such as "EXCELLENT", "GOOD", "NEED CARE", or "DANGER", a warning message such as "COMPLETE EXAMINATION REQUIRED", an indication of a face mark, or an equivalent indication may be displayed on the liquid crystal display screen 62D in accordance with the screening result.

Description on Various Embodiments of Power Source Section

In this section, various embodiments on the power source section are described. Considering the point that the inventive vital information measuring device is suitably used as a disposable pulse oximeter or a like device, it is desirable to simplify the arrangement of the vital information measuring device, for instance, to eliminate a component such as a measurement start switch. In view of this, it is desirable to configure the vital information measuring device in such a manner that energization i.e. power supply is started in response to a subject's attachment of the vital information measuring device onto a fingertip or a like site for automatic measurement. The configuration is also advantageous in suppressing consumption of the power source battery. In the following, various embodiments concerning the power source section which satisfy the above requirements are described.

Figure 16:
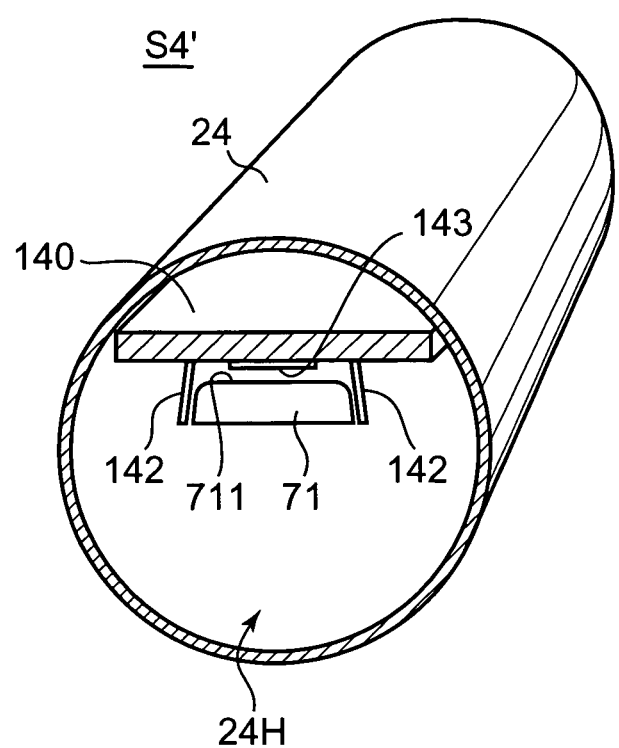
FIG. 16 is a perspective view showing a modified vital information measuring device in the fourth embodiment.

FIG. 16 is a perspective view showing a modified vital information measuring device "S4'" in the fourth embodiment. Similarly to the fourth embodiment, the vital information measuring device "S4'" is constructed in such a manner that an oblong flexible substrate 140 is housed in a fingerstall-like outer member 24. The vital information measuring device "S4'" has an improved arrangement for holding a power source battery 71, and is so configured as to allow the power source battery 71 to start a power supply to the respective sections of the functioning part mounted on the flexible substrate 140 in response to insertion of a fingertip of the subject into the vital information measuring device "S4'" through an opening 24H of the outer member 24.

Specifically, plastic deformable battery supports 142 are uprightly mounted on a battery holding surface of the flexible substrate 140. A power source terminal 143 is provided on a substrate surface of the flexible substrate 140 where the battery supports 142 are uprightly mounted. The battery supports 142 hold the power source battery 71 in a state that an electrode surface 711 of the power source battery 71 and the power source terminal 143 are disposed away from each other before the finger is inserted into the vital information measuring device "S4'".

When the fingertip is inserted through the opening 24H, the power source battery 71 is pressed upward by the fingertip, whereby the battery supports 142 are plastically deformed by application of the pressing force, and the electrode surface 711 of the power source battery 71 is contacted with the power source terminal 143. As a result of the operation, the power supply is started from the power source battery 71 to the respective sections of the functioning part. With this arrangement, automatic measurement can be started in response to insertion of the finger into the vital information measuring device "S4'", without providing a measurement start switch or a like device. It is desirable to form a proper adhesive layer near the contact site of the electrode surface 711 with the power source terminal 143 so as to prevent the electrode surface 711 from being detached from the power source terminal 143 after the contact, or to form a battery fixing groove to secure the contact of the electrode surface 711 with the power source terminal 143.

Figure 17:
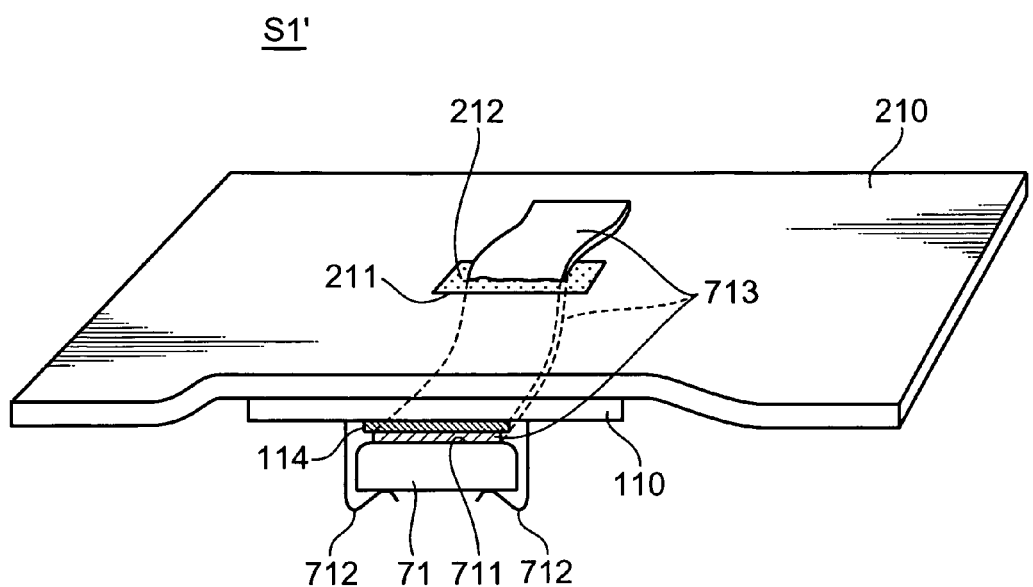
FIG. 17 is a perspective view showing a modified vital information measuring device in the first embodiment.

FIG. 17 is a perspective view showing a modified vital information measuring device "S1'" in the first embodiment. The vital information measuring device "S1'" includes an insulating sheet 713 for starting a power supply from a power source battery 71, in addition to a flexible substrate 110, an outer member 210, and a power source battery 71.

Battery support pins 712 are uprightly mounted on a battery holding surface of the flexible substrate 110. The battery support pin 712 has an urging force to urge the power source battery 71 against the flexible substrate 110. With this arrangement, an electrode surface 711 of the power source battery 71 is urged against a power source terminal 114 of the flexible substrate 110. The band-like insulating sheet 713 is provided between the electrode surface 711 and the power source terminal 114 for an electric insulation there between. A distal end of the insulating sheet 713 is drawn out onto an upper surface of the outer member 210 through a drawing slit 212 formed in the outer member 210, so that the user can easily pull out or draw out the insulating sheet 713 while nipping the distal end thereof. A self-adhesive compound is filled in the drawing slit 211 so that a clearance defined after the pulling out of the insulating sheet 713 can be filled.

In the vital information measuring device "S1'", pulling out the insulating sheet 713 at the time of starting measurement allows the electrode surface 711 to be contacted with the power source terminal 114 due to an urging operation of the power source battery 71 against the power source terminal 114 by the battery support pins 712. The contacts allows for start of the power supply from the power source battery 71 to the respective sections of the functioning part, thereby starting measurement by the vital information measuring device "S1'".

Figure 18A:
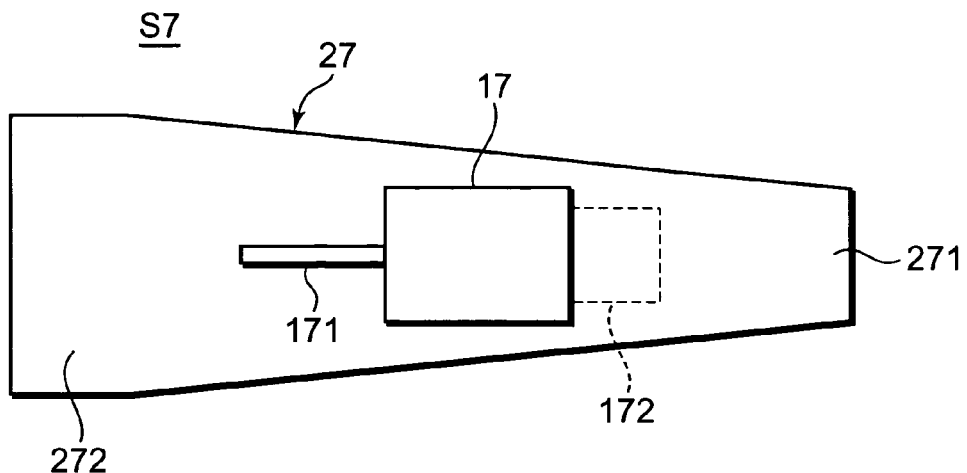
Figure 18B:
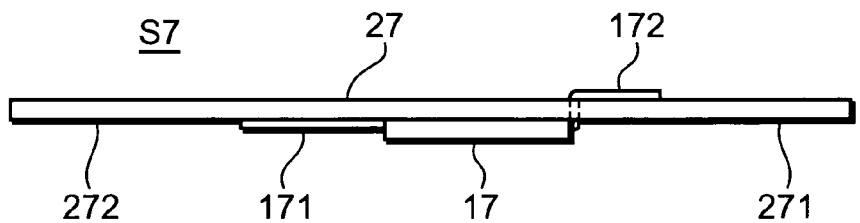
Figure 18C:
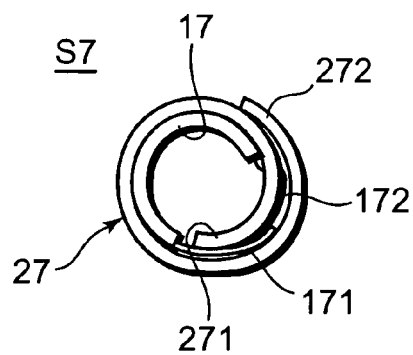

FIGS. 18A through 18C are diagrams showing a vital information measuring device "S7" according to a seventh embodiment of the invention, wherein FIG. 18A is a front view, FIG. 18B is a side view, and FIG. 18C is a side view showing a used state of the vital information measuring device "S7". The vital information measuring device "S7" includes a substantially rectangular flexible substrate 17, and an outer member 27 with one end thereof formed into a narrow width portion 271, and the other end thereof formed into a wide width portion 272.

The flexible substrate 17 includes a first electrode section 171 which extends from an unillustrated power source circuit and has a narrow width, and a second electrode section 172 having a wide width. The first electrode section 171 and the second electrode section 172 extend from opposing side portions of the flexible substrate 17, respectively. As shown in FIG. 18B, the first electrode section 171 extends toward the wide width portion 272 of the outer member 27 on a surface of the outer member 27 where the flexible substrate 17 is mounted. The second electrode section 172 extends toward the narrow width portion 271 through the outer member 27. Although a detailed description on a circuit configuration of the flexible substrate 17 is omitted, electrical conduction between the first electrode section 171 and the second electrode section 172 allows for a power supply from an unillustrated power source battery to respective sections of a functioning part of the vital information measuring device "S7".

As shown in FIG. 18C, the vital information measuring device "S7" having the above construction is wound around a fingertip or a like portion in such a manner that the narrow width portion 271 is placed inside relative to the wide width portion 272 when in use. The winding places the first electrode section 171 outside relative to the second electrode section 172, thereby making the first electrode section 171 and the second electrode section 172 conductive to each other. With this arrangement, the power supply from the power source battery to the respective sections of the functioning part is started, thereby starting measurement by the vital information measuring device "S7".

Figure 19:
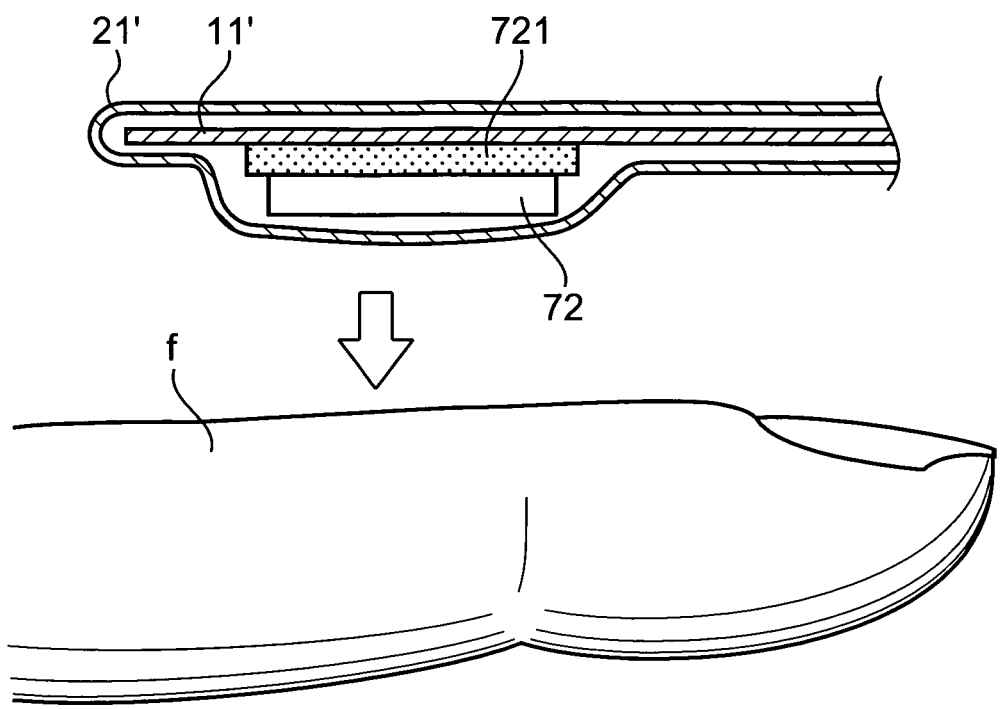
FIG. 19 is a cross-sectional view showing an embodiment using a body temperature powered battery.

Further, it is possible to configure the vital information measuring device in such a manner that measurement is started in response to supply of heat energy by contact with a human body by providing the heat power generator mentioned in the foregoing section of "Description on Basic Embodiment", in place of adopting the mechanical mechanism using the power source battery. FIG. 19 is a cross-sectional view showing an example of the arrangement, wherein a body temperature powered battery 72 is mounted on a flexible substrate 11', and the flexible substrate 11' is sealably closed by an outer member 21'.

The body temperature powered battery 72 is a device equipped with a thermoelectric conversion device, and is adapted to generate a power based on Seebeck effect, utilizing a difference in temperature between an area of the body temperature powered battery 72 which is heated by the body temperature of the subject due to a contact with a part of the subject's body, and an area thereof away from the body part. The body temperature powered battery 72 is mounted on a heat insulating plate 721 to avoid thermal influence from the flexible substrate 11'. Contact of the body temperature powered battery 72 with the finger "f" to be measured heats the body temperature powered battery 72 by the body temperature of the subject, thereby generating a power. Thus, measurement can be started in response to the subject's wearing the vital information measuring device.

Figure 20:
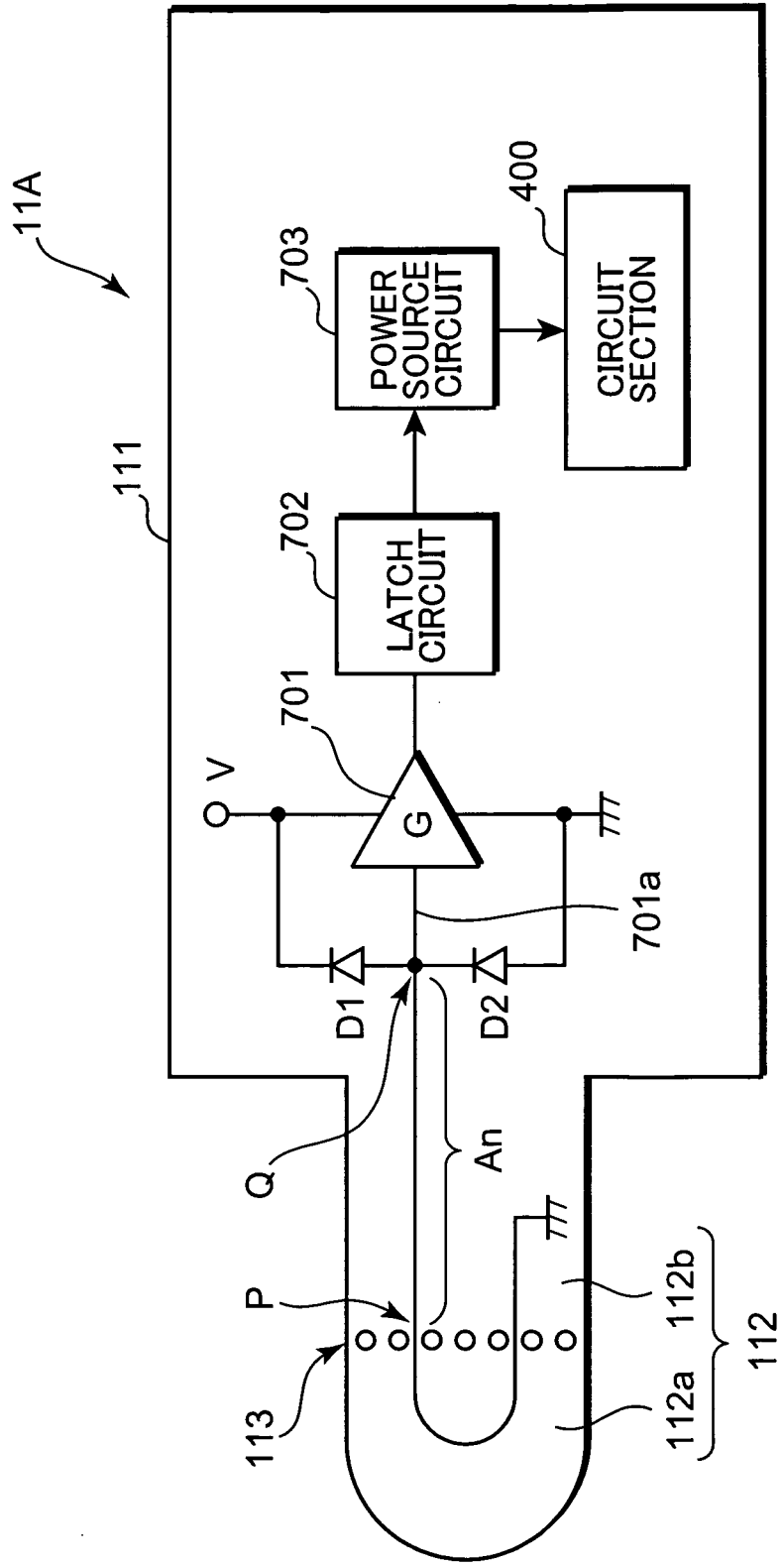
FIG. 20 is a block diagram showing a flexible substrate provided with a circuit arrangement of realizing an embodiment equipped with an easily breakable portion.

In addition to the above arrangement, a part of a flexible substrate may be formed into an easily breakable portion, so that a power supply to the respective sections of the functioning part is started or suspended by breaking the easily breakable portion. FIG. 20 is a block diagram showing a flexible substrate 11A equipped with a circuit configuration of realizing an embodiment provided with the easily breakable portion.

The flexible substrate 11A includes a substrate main body 111, and an extension 112 extending from a side portion of the substrate main body 111. A perforation portion 113, which corresponds to an array of sequential through-holes, and serves as an easily breakable portion, is formed in the extension 112. The extension 112 is dividable into a distal portion 112a and a base end 112b by the perforation portion 113.

A buffer gate 701, a latch circuit 702, a power source circuit 703, and a circuit section 400 corresponding to the measurement circuit section 41, the main controller 42, and the like are mounted on the flexible substrate 11A. The buffer gate 701 has a gate IC. An input line 701a of an input section "Q" of the buffer gate 701 has a relatively long linear portion extending to the distal portion 112a over the perforation portion 113 of the extension 112, and is folded backward and connected to the ground at the base end 112b over the perforation portion 113. Diodes D1 and D2 provided in the input section "Q" are protective diodes for the buffer gate 701.

The latch circuit 702 supplies an output depending on an output "L" or "H" of the buffer gate 701 to the power source circuit 703. This embodiment adopts an arrangement that the output of the latch circuit 702 is fixed to "H" instantaneously when the output of the buffer gate 701 is changed from "L" to "H". The power source circuit 703 is turned on depending on the output of the latch circuit 702 to supply a drive voltage to the circuit section 400. For instance, the power source circuit 703 is controllably turned on in response to supply of the output "H" from the latch circuit 702.

With the flexible substrate 11A having the above construction, when the distal portion 112a is detached from the rest of the flexible substrate 11A at the perforation portion 113, a portion from the input section "Q" to a distal end "P", which is formed by detachment of the distal portion 112a, of the input line 701a of the buffer gate 701 is electrically disconnected from the ground. Since the portion from "P" to "Q" has a relatively long length, the portion from "P" to "Q" also functions as an antenna portion "An" for picking up electric induction noise. As a result, an unstable input potential is supplied from the antenna portion "An" to the input section "Q" of the buffer gate 701, which may resultantly cause an exceedingly large input threshold value for the buffer gate 701. As a result, the output of the buffer gate 701 is changed from "L" to "H", and the latch circuit 702 is fixed to the output "H" in response to the output change. Then, the power source circuit 703 is turned on in response to the output "H" of the latch circuit 702, whereby a drive voltage is supplied to the circuit section 400 thereafter. Even if the antenna portion "An" picks up induction noise after the drive voltage supply, there is no likelihood that the power source circuit 703 may be turned off, because the output of the latch circuit 702 is fixed.

Figure 21:
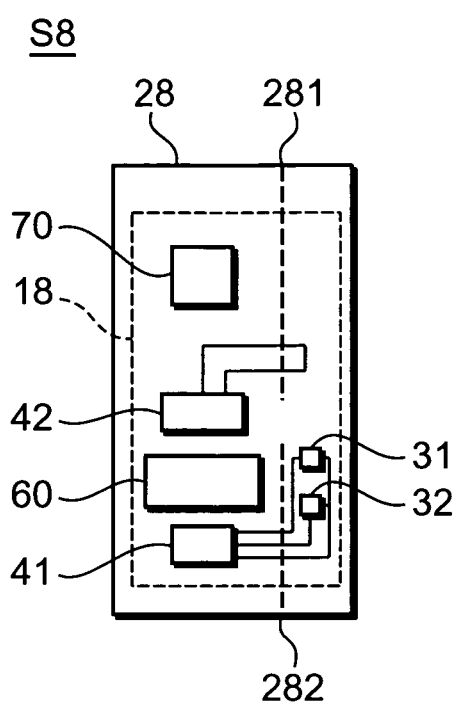
FIG. 21 is a plan view showing a vital information measuring device according to an eighth embodiment of the invention.

Use of the flexible substrate 11A having the above configuration enables to start measurement by the vital information measuring device by breaking the easily breakable portion partially formed in the flexible substrate 11A. FIG. 21 is a plan view showing a vital information measuring device "S8" equipped with an example of the easily breakable structure, according to an eighth embodiment of the invention. The vital information measuring device "S8" is composed of a flexible substrate 18 on which various components of a functioning part such as a light emitter 31, a light detector 32, a measurement circuit section 41, a main controller 42, a display section 60, and a power source section 70 are mounted; and an outer member 28 for enclosing the flexible substrate 18. The vital information measuring device "S8" is further provided with a first perforation portion 281 and a second perforation portion 282, as an example of the easily breakable portion.

Similarly to the perforation portion 113 in FIG. 20, the first perforation portion 281 is a detaching portion for enabling start of a power supply from the power source section 70 to the functioning part by breaking the outer member 28 at the first perforation portion 281. The second perforation portion 282 is a detaching portion for electrically disconnecting the light emitter 31 and the light detector 32 from the measurement circuit section 41. Specifically, detaching a part of the outer member 28 from the rest of the outer member 28 at the second perforation portion 282 prohibits a light emission operation by the light emitter 32 and a light receiving operation by the light detector 32, whereby a measurement operation is suspended.

Figure 22A:
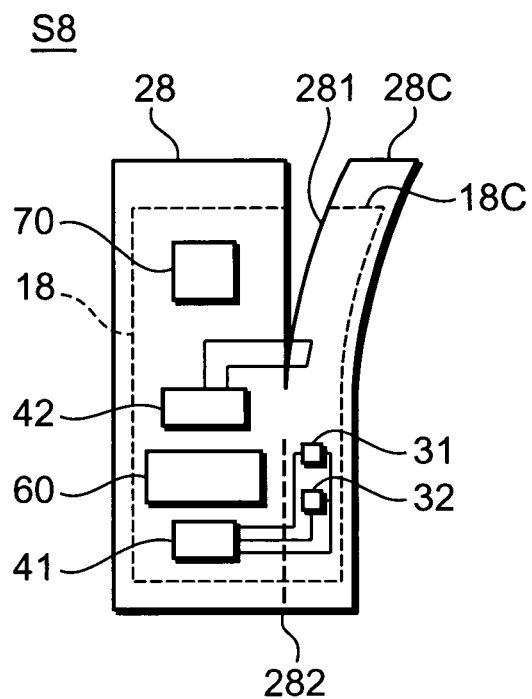
FIGS. 22A and 22B are plan views for explaining how the vital information measuring device in the eighth embodiment is used.

In the vital information measuring device "S8" having the above construction, the first perforation portion 281 and the second perforation portion 282 are not detached from the rest of the outer member 28 in an initial state of use i.e. in the state shown in FIG. 21. Accordingly, in this state, a drive voltage is not supplied from the power source section 70 to the respective sections of the functioning part of the flexible substrate 18. Then, as shown in FIG. 22A, when the outer member 28 is broken into two parts by the first perforation portion 281, a part 18C of the flexible substrate 18 is detached from the rest of the flexible substrate 18. The detachment allows the power source section 70 to start supply of a drive voltage to the respective sections of the functioning part based on the principle described referring to FIG. 20, whereby a measurement operation is started. At this time, by winding a band-like portion 28C (see FIG. 22A) of the outer member 28 around a fingertip or a like site of the subject, the vital information measuring device "S8" can be removably attached to the fingertip or a like portion.

Figure 22B:
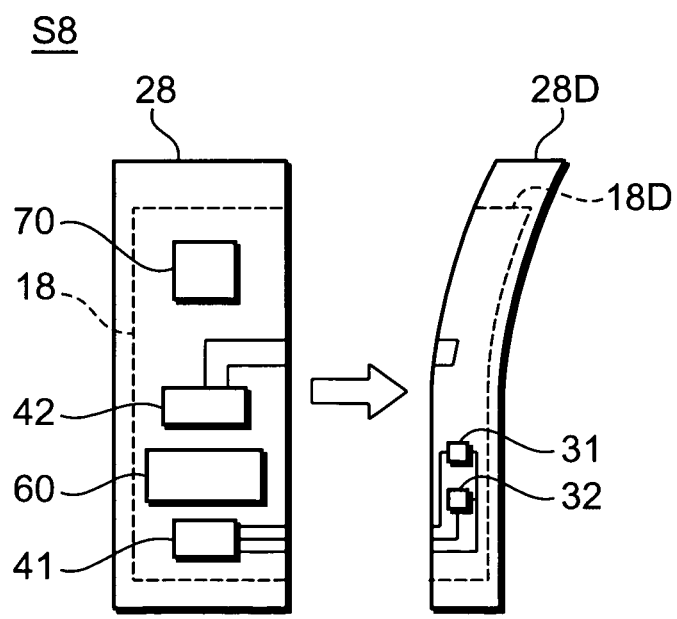

Then, after completion of the measurement for a certain measurement period, as shown in FIG. 22B, further breaking the outer member 28 into two parts by the second perforation portion 282, which means detaching a part 18D from the rest of the flexible substrate 18, and detaching a part 28D from the rest of the outer member 28, respectively, enables to suspend the drive signal supply to the light emitter 31 and to the light detector 32, whereby the measurement operation is forcibly terminated. In this arrangement, it is desirable not to disconnect a circuit wiring of connecting the display section 60 to the power source section 70 so as to continue a displaying operation by the display section 60. The vital information measuring device "S8" having the above arrangement enables to start and suspend a measurement operation i.e. a power supply operation in response to detachment of the necessary parts from the rest of the flexible substrate 18 and from the outer member 28 by the first perforation portion 281 and the second perforation portion 282, as easily breakable portions, at respective appropriate timings.

Description on other Various Embodiments

As shown in FIG. 2, the flexible substrate 11 may preferably have the communication section 80 for performing data communication with another electrical apparatus such as a personal computer. In the arrangement, the communication section 80 is required to have a connector portion to be connected to a communication cable terminal, a wireless communication portion, or the like.

Figure 23A:
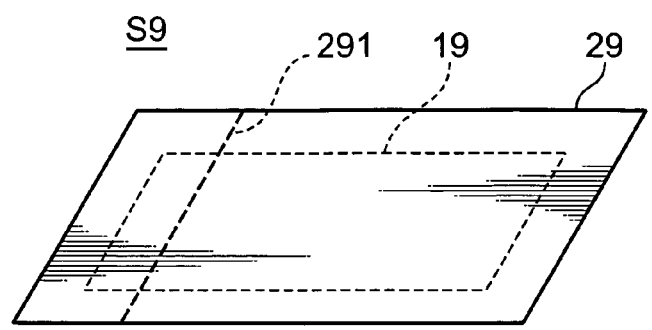
FIGS. 23A and 23B are perspective views showing a vital information measuring device according to a ninth embodiment of the invention.
Figure 23B:
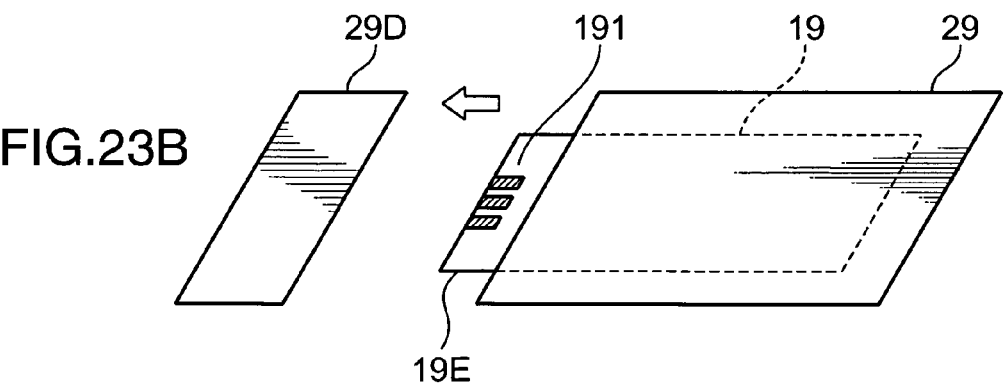

FIGS. 23A and 23B are perspective views showing a vital information measuring device "S9" equipped with a connector portion, according to a ninth embodiment of the invention. As shown in FIG. 23A, the vital information measuring device "S9" includes a flexible substrate 19, and an outer member 29 for enclosing the flexible substrate 19. A perforation portion 291 is formed exclusively on the outer member 29.

In the vital information measuring device "S9", as shown in FIG. 23B, when measurement is completed, detaching an end portion 29D from the rest of the outer member 29 by the perforation portion 291 allows an end portion 19E of the flexible substrate 19 to be exposed, with the result that a connector portion 191 including a conductive exposed portion formed on the end portion 19E is exposed. Connecting the exposed connector portion 191 to a communication cable provided with a clip connector, for instance, allows for data communication between the vital information measuring device and a personal computer or a like apparatus.

Description on other Examples of Vital Information Measuring Device

<RR Interval Measuring Device>

In the foregoing, the various embodiments of the vital information measuring device of the invention are described by the example of the pulse oximeter. Alternatively, the invention is applicable to a vital information measuring device other than the above embodiments. For instance, an electrocardiographic RR interval measuring device can be provided as an example of the inventive vital information measuring device. The RR interval is a peak-to-peak interval of two consecutive R waves, which are the most frequently observed waves among P waves, Q waves, R waves, S waves, and T waves, which appear in one cycle of heartbeat in an electrocardiogram. Expressing the RR interval in a time-series manner enables to find out a heartbeat fluctuation. The heartbeat fluctuation is widely and clinically used as an index for assessing a biological control function of an autonomic nervous system involved in an organic activity of the body.

In the above modification, electrodes for detecting an action potential of a heart are used as the sensor section 30 shown in FIG. 1. Alternatively, a pulse wave detector using a light emitter for emitting light of a single wavelength may be used, in place of the light emitter 31 using a two-wavelength LED described referring to FIG. 2, in order to extract information corresponding to the RR intervals i.e. peak-to-peak intervals concerning a pulse wave, out of pulse wave data. Use of the RR interval measuring device is advantageous in remarkably reducing stress of the subject involved in wearing the device, as compared with the conventional holter monitor. A relatively long time measurement for about one to two weeks is required in measuring atrial fibrillation. However, with the altered arrangement, the long time measurement can be conducted with less stress or discomfort to a subject.

<PSG Device>

A PSG (polysomnography) device for detecting assessment parameters such as electroencephalographic waveforms, air flow rates through mouth or nose, snoring sounds, chest and abdominal movements in respiration, and body positions/body movements is used to obtain AHI (apnea hypopnea index), which indicates the number of apneustic breathings or infrequent breathings per hour. In the conventional PSG device, sensors for acquiring the assessment parameters are attached to certain body sites of a subject, and the sensors and the PSG device main body are connected by cables. In the arrangement, the subject is even deprived of freedom of rolling over during the PSG measurement.

Figure 24:
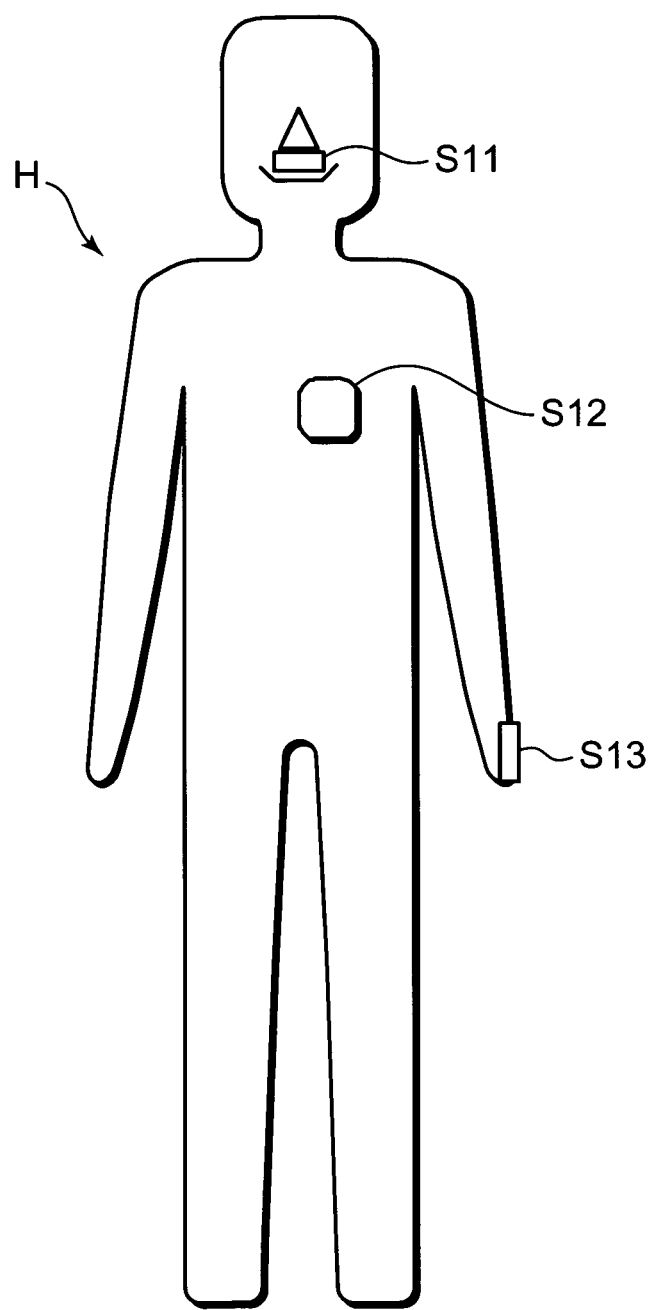
FIG. 24 is a diagram showing an embodiment to be used as a polysomnography device.
Figure 25:
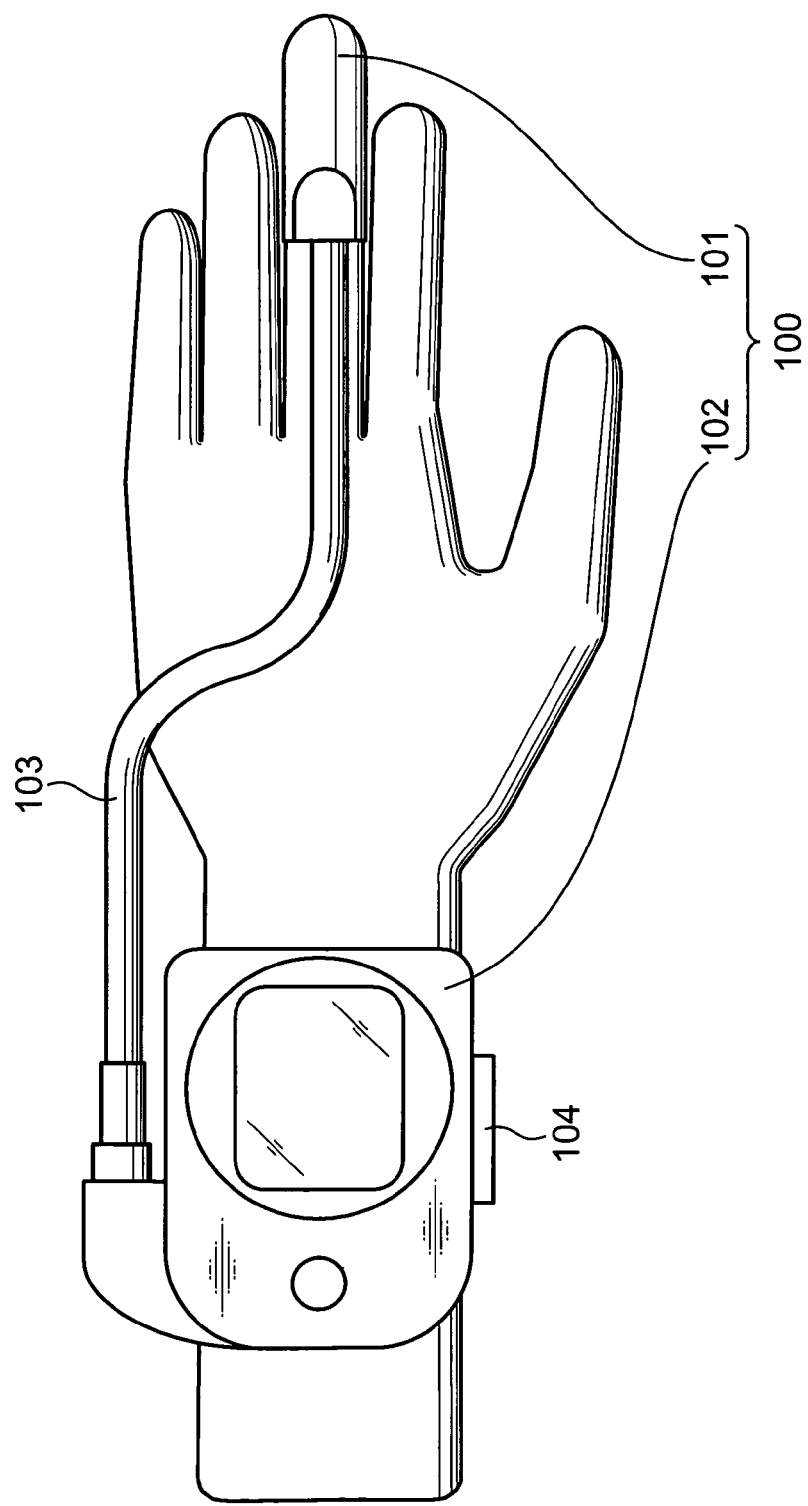
FIG. 25 is a diagram showing how a conventional pulse oximeter is mounted.

Application of the inventive vital information measuring device to the PSG measurement is advantageous in remarkably reducing stress of the subject involved in wearing the device. For instance, as shown in FIG. 24, a first vital information measuring device "S11" as an air flow sensor for detecting air flow rates through mouth or nose, a second vital information measuring device "S12" as a sensor for detecting chest and abdominal movements in respiration, and a third vital information measuring device "S13" as a pulse oximeter for measuring $SpO_2$ are prepared, and are removably attached to predetermined body sites of a subject, respectively. In this arrangement, a temperature sensor is used as a sensor section of the first vital information measuring device "S11", an acceleration sensor or a distortion gauge is used as a sensor section of the second vital information measuring device "S12", and the aforementioned flexible substrate provided with the light emitter and the light detector is used in the third vital information measuring device "S13". Measurement values obtained from the first, the second, and the third vital information measuring devices "S11", "S12", and "S13" are stored in memory sections of the respective vital information measuring devices in association with measurement time information. Data analysis is conducted while correlating the respective measurement data with the measurement time information. Thus, analysis data such as AHI can be obtained.

The aforementioned embodiments essentially include the invention having the following arrangements.

A vital information measuring device according to an aspect of the invention comprises a flexible substrate including a functioning part which is mounted thereon; and an outer member for covering the flexible substrate. The functioning part includes: a sensor section for sequentially measuring a parameter relating to certain vital information on a subject; a circuit section for performing a predetermined process with respect to a measurement signal outputted from the sensor section; a memory section for storing therein the measurement signal or measurement data after the process by the circuit section; a display section for displaying thereon certain information relating to the measurement; and a power source section for supplying a drive voltage to the respective sections of the functioning part.

In the above arrangement, the sensor section, the circuit section, the memory section, the display section, and the power source section, which constitute the functioning parts required for measuring the vital information, are mounted on the single flexible substrate. This arrangement eliminates the need of a cable for electrically connecting the sensor section to the device main body, or a mechanism for performing radio communication between the sensor section and the device main body, as required in the conventional art. Also, the arrangement protects the flexible substrate, using the outer member.

According to the above arrangement, the sensor section and the device main body are not separated from each other, unlike the conventional arrangement. This eliminates the need of a connection cable or a radio communication mechanism, thereby simplifying the arrangement. Also, there is no likelihood that the cable may be entangled. Thus, the arrangement can remarkably reduce stress of the subject involved in wearing the device. This enables to provide a vital information measuring device which is suitable for a long time vital information measurement, and has an enhanced operability. Also, since the flexible substrate is used, the device provides fittability to a curved measuring site or a distal body part such as a fingertip. Further, since the arrangement can be made simple, the arrangement is advantageous in reducing the production cost of the vital information measuring device, which enables to provide a disposable vital information measuring device.

In the above arrangement, preferably, the circuit section may have an A/D converter for converting the measurement signal into a digital signal, and an analysis processor for performing a predetermined data analysis process with respect to the digital signal. In the arrangement, the functioning part mounted on the flexible substrate is provided with the data analysis processing function. Allowing the display section to display an analysis result of the analysis processor enables the subject to easily and promptly known a disease or the like.

According to the arrangement, since the subject can promptly know the analysis result relating to the measured vital information, home-based screening is available, thereby enabling to provide a vital information measuring device useful in finding a disease at an early stage thereof.

Preferably, the circuit section may have a main controller for controlling operations of the functioning part, and the main controller may control at least one of the operations including measuring the vital information of the subject by the sensor section, recording the measurement signal or the measurement data into the memory section in association with measurement time information, and displaying ongoing measurement status information or certain information relating to the measured vital information by the display section.

In the above arrangement, since the main controller controls the at least one operation out of the measuring operation, the recording operation, and the display operation by the functioning part, a user-friendly vital information measuring device is provided.

In any one of the above arrangements, preferably, the sensor section may have a light emitter and a light detector, and the outer member may be a member having a light blocking function. In the case where the sensor section provided with the light emitter and the light detector performs an optical measurement to measure a blood oxygen saturation, a pulse waveform, or the like, the arrangement prevents external light from affecting the measurement because the outer member has the light blocking function.

According to the above arrangement, in the case where the optical measurement is conducted by the sensor section, intrusion of the external light resulting in measurement error can be prevented, thereby ensuring accurate measurement.

In any one of the above arrangements, preferably, the vital information to be measured may include at least one vital information selected from blood oxygen saturations, pulse waveforms, air flow rates through mouth or nose, snoring sounds, body positions/body movements, chest and abdominal movements in respiration, and electrocardiographic waveforms.

According to the above arrangement, the assessment parameter which has been measured by the conventional PSG device can be measured by the vital information measuring device, and a medical diagnosis substantially equivalent to a medical diagnosis by the conventional PSG device is enabled based on the measurement result.

In any one of the above arrangements, preferably, the display section may have an LED display device for performing a lighting operation in association with ongoing measurement status information or measured vital information. In the arrangement, the ongoing measurement status information or the measured vital information is displayed by the lighting operation of the LED (light emitting diode).

According to the above arrangement, since the measurement status, the analysis result on the vital information, or the like can be displayed on the simplified display section using the LED display device, the arrangement provides a vital information measuring device with an enhanced operability and with a less cost.

In any one of the arrangements, preferably, the display section may have a flexible liquid crystal display device for displaying indication information in association with ongoing measurement status information or measured vital information. In the arrangement, the ongoing measurement status information or the measured vital information is displayed by the flexible liquid crystal display device.

According to the above arrangement, since the flexible liquid crystal display device is used, the measurement status, the analysis result on the vital information, or the like can be displayed in a refine manner on the liquid crystal display device. Also, this arrangement secures fittability even if the vital information measuring device is removably attached to a curved measuring site or a distal body part such as a fingertip.

In any one of the above arrangements, preferably, the power source section may have a power generator for generating an electric power, utilizing heat energy of a human body.

According to the above arrangement, since the heat energy of the human body is utilized for power generation, the arrangement is free from providing the battery in the power source section. Also, in response to mounting the vital information measuring device onto the subject, the body temperature of the subject is sensed to start the power generation, and the measurement can be started based on the power generation. This provides an enhanced operability.

In any one of the above arrangements, preferably, the power source section may have a battery, and a drawable insulating sheet may be provided between an electrode of the battery and a circuit wiring terminal for supplying an electric power. In the arrangement, pulling out or drawing out the insulating sheet enables to start a power supply from the power source section to the respective sections of the functioning part.

The above arrangement enables to provide a vital information measuring device designed in such a manner as to start measuring the vital information in response to pulling out or drawing out the insulating sheet.

In any one of the above arrangements, preferably, a part of the flexible substrate may be formed into an easily breakable portion, a part of a circuit wiring may be wired in such a manner as to cross the easily breakable portion, and a power supply to the respective sections of the functioning part may be started or suspended by breaking the flexible substrate by the easily breakable portion. In the arrangement, the power supply is started or suspended in response to breaking of the flexible substrate by the easily breakable portion. This eliminates the need of mounting a component such a measurement start switch onto the flexible substrate, thereby constructing the vital information measuring device in a more simplified manner.

In any one of the above arrangements, preferably, the outer member may be a member having a waterproof function to make the flexible substrate waterproof.

According to the above arrangement, since the flexible substrate is made waterproof, the subject is not only allowed to take a bath or a like action while wearing the vital information measuring device, but also to measure the vital information before and after the bathing, which involves a relatively large change in body temperature of the subject, as well as during the bathing. Also, the arrangement is advantageous in preventing an electrical leakage or the like, which may occur in a condition that the sensor section includes electrodes for contacting with a body surface, as required in measuring an electrocardiographic waveform.

Further preferably, the outer member may have an adhesive layer having an adhesion to a human skin.

The above arrangement enables to removably attach the vital information measuring device onto the body part of the subject, using the adhesive layer. This enables to enhance the operability, and further reduce stress of the subject involved in wearing the vital information measuring device.

In any one of the arrangements, preferably, the outer member may have a support structure for integrally and detachably supporting the flexible substrate. In the arrangement, the flexible substrate is supported by the support structure provided on the outer member, thereby integrally forming the flexible substrate with the outer member.

The above arrangement enables to easily and detachably attach the flexible substrate to the outer member, thereby enhancing the operability.

In the above arrangement, preferably, the outer member may be integrally formed with a locking member for fixedly attaching the outer member to a body part of the subject. In the arrangement, fixedly attaching the locking member of the outer member to a predetermined site e.g. a fingertip of the subject for the vital information measurement, enables to mount the flexible substrate to an intended site. This allows the subject to easily and removably attach the vital information measuring device at home or a like place.

Preferably, in the case where the outer member is removably attached to a finger of the subject, and the display section has a transversely oblong display screen, the flexible substrate may be supported on the outer member in such a manner as to make a longitudinal direction of the display screen substantially coincident with an extending direction of the finger when the outer member is removably attached to the finger.

According to the above arrangement, viewability of the display screen is enhanced in a case that the vital information measuring device is removably attached to the finger of the subject.

In any one of the above arrangements, preferably, at least the display section may be mounted on one surface of the flexible substrate, and the sections other than the display section of the functioning part may be mounted on the other surface of the flexible substrate, and the outer member may be formed with a window portion through which the display screen is viewable. In the arrangement, the display section is mounted on the one surface of the flexible substrate, and the display section is viewable through the window portion.

The above arrangement enables to increase the area of the display section, as compared with a case that all the sections constituting the functioning part are mounted on the one surface of the flexible substrate. This enhances the viewability of the display section.

In any one of the above arrangements, preferably, the flexible substrate may be mounted thereon with a communication section for performing data communication with another electrical apparatus. In the arrangement, after the measurement completion, data concerning the measured vital information or the analysis data is transferable to the another electrical apparatus such as a personal computer through the communication section.

According to the above arrangement, more sophisticated data analysis or the like can be performed by transferring the vital information data or the analysis data to the another electrical apparatus such as the personal computer.

Preferably, the communication section may have a connector portion for electrically connecting the vital information measuring device to the another electrical apparatus, and the connector portion may be exposed by partly breaking the outer member.

According to the above arrangement, the connector portion is protected by the outer member until the measurement completion, and after the measurement completion, the connector portion is exposed by partly breaking the outer member in transferring the measurement data or the like to the another electrical apparatus. This enhances the operability of the user.

Although the present invention has been fully described by way of example with reference to the accompanying drawings, it is to be understood that various changes and modifications will be apparent to those skilled in the art. Therefore, unless otherwise such changes and modifications depart from the scope of the present invention hereinafter defined, they should be construed as being included therein.

What is claimed is:

1. A vital information measuring device comprising:
a flexible substrate comprising a flexible base member constructed in such a manner that a conductive pattern made of an electric conductor is fabricated on a plastic film, including a functioning part which is mounted thereon; and
an outer member that is mounted to and substantially covers at least one side of the flexible substrate including the conductive pattern side,
the functioning part including:
a sensor section that is configured to sequentially measure a parameter relating to certain vital information on a subject;
a circuit section that is configured to perform a predetermined process with respect to a measurement signal outputted from the sensor section, the circuit section including a main controller that is configured to control operations of the functioning part, the main controller being configured to control at least one of the operations including:
measuring the vital information of the subject by the sensor section, and
recording the measurement signal or the measurement data into the memory section together with measurement time information for such measurement signal or the measurement data;
a memory section for storing therein the measurement signal or measurement data together with measurement time information after the process by the circuit section;
a display section for displaying thereon certain information relating to the measurement; and
a power source section for supplying a drive voltage to the respective sections of the functioning part,
wherein said outer member is composed of an at least partially transparent material in order to permit visual inspection of the information displayed on the display section;
the outer member is a member having a light-blocking function and a flexibility; and
the outer member had an adhesive layer adapted to adhere to human skin; and
the outer member prevents the conductive pattern from contacting human skin.

2. The vital information measuring device according to claim 1, wherein
the circuit section has an A/D converter for converting the measurement signal into a digital signal, and
an analysis processor that is configured to perform a predetermined data analysis process with respect to the digital signal.

3. The vital information measuring device according to claim 1, wherein
the sensor section has a light emitter and a light detector.

4. The vital information measuring device according to claim 1, wherein
the vital information to be measured includes at least one vital information selected from blood oxygen saturations, pulse waveforms, air flow rates through mouth or nose, snoring sounds, body positions/body movements, chest and abdominal movements in respiration, and electrocardiographic waveforms.

5. The vital information measuring device according to claim 1, wherein
the display section has a flexible liquid crystal display device for displaying indication information in association with ongoing measurement status information or measured vital information.

6. The vital information measuring device according to claim 1, wherein
the outer member is a member having a waterproof function to make the flexible substrate waterproof.

7. The vital information measuring device according to claim 1, wherein
the outer member has a support structure for integrally and detachably supporting the flexible substrate.

8. The vital information measuring device according to claim 1, wherein
the outer member is configured to be removably attached to the finger of a subject such that in the case where the outer member is removably attached to a finger of the subject, and the display section has a transversely oblong display screen, the flexible substrate is supported on the outer member in such a manner as to make a longitudinal direction of the display screen substantially coincident with an extending direction of the finger.

9. The vital information measuring device according to claim 1, wherein
at least the display section is mounted on a surface of the flexible substrate that faces the outer member, and the sections other than the display section of the functioning part are mounted on the other surface of the flexible substrate, and
the outer member is formed with a window portion through which the display screen is viewable.

10. The vital information measuring device according to claim 1, wherein
the sensor section is configured to sequentially and repeatedly measure a parameter relating to certain vital information on a subject and the circuit section is configured to perform a predetermined process with respect to repeated measurement signals outputted from the sensor section and the main controller is configured to record a plurality of repeated measurement signals or repeated measurement data into the memory section together with measurement time information for each of such repeated measurement signals or repeated measurement data.

11. A vital information measuring device comprising:
a flexible substrate comprising a flexible base member constructed in such a manner that a conductive pattern made of an electric conductor is fabricated on a plastic film, including a functioning part which is mounted thereon; and
an outer member that is mounted to and substantially covers at least one side of the flexible substrate including the conductive pattern side,
the functioning part including:
a sensor section that is configured to sequentially measure a parameter relating to certain vital information on a subject;
a display section for displaying thereon certain information relating to the measurement;
a circuit section having a main controller that is configured to control operations of the functioning part including measuring the vital information of the subject by the sensor section recording the measurement signal or the measurement data into the memory section in association with measurement time information, and causing the display of ongoing measurement status information or certain information relating to the measured vital information by the display section;

a memory section for storing therein the measurement signal or measurement data after the process by the circuit section; and a power source section for supplying a drive voltage to the respective sections of the functioning part;

wherein the display section is mounted on a surface of the flexible substrate that faces the outer member, and the sections other than the display section of the functioning part are mounted on the other surface of the flexible substrate, and the outer member is formed with a window portion through which the display screen is viewable; and the outer member is a member having a light-blocking function; and the outer member prevents the conductive pattern from contacting human skin.

12. The vital information measuring device according to claim 11, wherein the main controller is configured to control operations of the functioning part so as to cyclically repeat measuring the vital information of the subject by the sensor section and to record a plurality of repeated measurement signals or repeated measurement data into the memory section in association with measurement time information for each of said repeated measurement signals or repeated measurement data.

\* \* \* \* \*